United States Patent
Nakagawa et al.

(10) Patent No.: US 11,841,364 B2
(45) Date of Patent: Dec. 12, 2023

(54) METHOD FOR ACQUIRING INFORMATION ON RESPIRATORY INFECTION

(71) Applicant: SYSMEX CORPORATION, Kobe (JP)

(72) Inventors: Atsushi Nakagawa, Kobe (JP); Takehiro Hasegawa, Kobe (JP); Kohjin Suzuki, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 76 days.

(21) Appl. No.: 17/507,867

(22) Filed: Oct. 22, 2021

(65) Prior Publication Data

US 2022/0128548 A1 Apr. 28, 2022

(30) Foreign Application Priority Data

Oct. 22, 2020 (JP) ................................. 2020-177439

(51) Int. Cl.
*G01N 33/543* (2006.01)
*A61K 45/06* (2006.01)
*G01N 33/58* (2006.01)

(52) U.S. Cl.
CPC ....... *G01N 33/54326* (2013.01); *A61K 45/06* (2013.01); *G01N 33/581* (2013.01); *G01N 2800/12* (2013.01); *G01N 2800/347* (2013.01); *G01N 2800/50* (2013.01); *G01N 2800/60* (2013.01)

(58) Field of Classification Search
CPC .. A61K 45/06; G01N 33/581; G01N 2800/12; G01N 2800/347; G01N 2800/50; G01N 2800/60
See application file for complete search history.

(56) References Cited

U.S. PATENT DOCUMENTS 7,141,382 B1 * 11/2006 Parikh ................ G01N 33/6869 435/7.1
2005/0251873 A1 * 11/2005 Penninger .......... C12N 15/8509 435/456

FOREIGN PATENT DOCUMENTS

JP 01-254868 A 10/1989

OTHER PUBLICATIONS

Foronjy (PLoS One 2014 9:e90567). (Year: 2014).*
Huan Han et al., "Profiling serum cytokines in COVID-19 patients reveals IL-6 and IL-10 are disease severity predictors", Emerging Microbes & Infections, 2020, pp. 1123-1130, vol. 9.
Tahmineh Mokhtari et al: "COVID-19 and multiorgan failure: A narrative review on potential mechanisms", Journal of Molecular Histology, Published online on Oct. 4, 2020, vol. 51, No. 6, pp. 613-628, Springer.
Kaviyarasi Renu et al: "Coronaviruses pathogenesis, comorbidities and multi-organ damage—A review", Life Sciences, 2020, vol. 255, Article No. 117839, 15 pages, Elsevier.
Paul Gabarre et al: "Acute kidney injury in critically ill patients with COVID-19", Intensive Care Medicine, Published online on Jun. 12, 2020, vol. 46, No. 7, pp. 1339-1348, Springer.
Takehiro Hasegawa et al: "Type 1 inflammatory endotype relates to low compliance, lung fibrosis, and severe complications in COVID-19", Cytokine, 2021, vol. 148, Article No. 155618, 9 pages, Elsevier.
Tony Tien et al: "MP58-13 Recurrent Urological Hospital Attendances: How Do We Improve the Patient Care to Reduce Reattendance?", Ildar Kabirov et al: "MP58-14 Clinical Significance of Markers of Acute Renal Injury in Predicting Adverse Outcomes in Patients With Coronavirus Infection", The Journal of Urology, Sep. 13, 2021, vol. 206, No. 3S, Supplement, p. e993.
Guyi Wang et al: "C-Reactive Protein Level May Predict the Risk of COVID-19 Aggravation", Open Forum Infectious Diseases, 2020, vol. 7, No. 5, 5 pages, Oxford University Press.
Extended European search report dated Mar. 18, 2022 in a counterpart European patent application No. 21204089.3.

* cited by examiner

*Primary Examiner* — Changhwa J Cheu
(74) *Attorney, Agent, or Firm* — Sughrue Mion, PLLC

(57) ABSTRACT

Disclosed is a method for acquiring information on respiratory infection, the method including measuring at least one biomarker in a specimen collected from a subject suffering from respiratory infection, or from a subject suspected of having the respiratory infection, in which the biomarker includes at least one selected from the group consisting of CXCL9, CCL3, and IL-18, and a measured value of the biomarker can serve as an index of a risk of causing acute kidney injury or pulmonary fibrosis following respiratory infection.

12 Claims, 14 Drawing Sheets

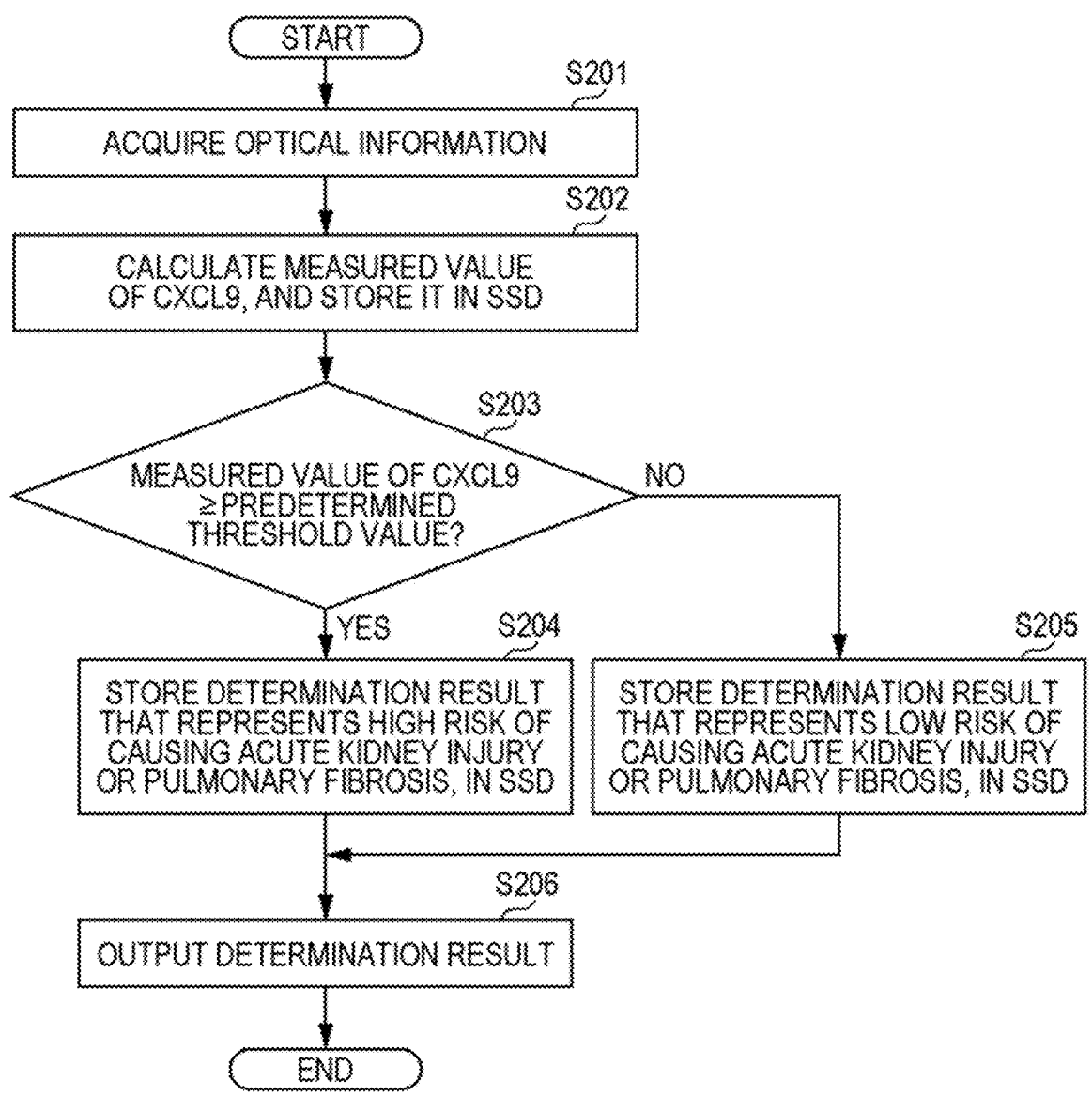

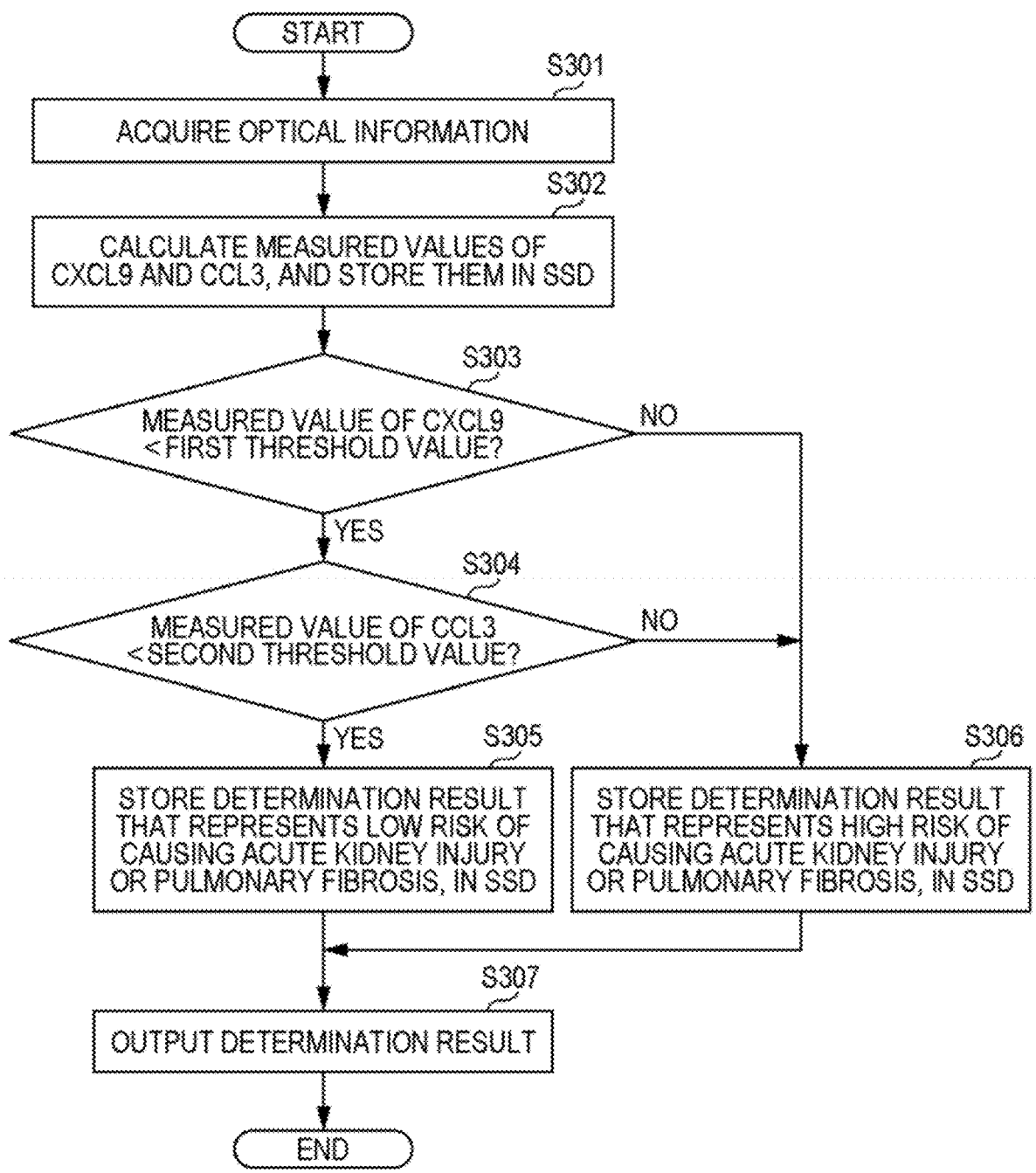

METHOD FOR ACQUIRING INFORMATION ON RESPIRATORY INFECTION

CROSS REFERENCE TO RELATED APPLICATIONS

This application claims priority from prior Japanese Patent Application No. 2020-177439, filed on Oct. 22, 2020, entitled "Method for Acquiring information on Respiratory Infection, Method for Monitoring Measured Value of Biomarker, Reagent Kit, Apparatus for Acquiring information on Respiratory Infection, and Computer Program Product", the entire contents of which are incorporated herein by reference.

FIELD OF THE INVENTION

The present invention relates to a method for acquiring information on respiratory infection.

BACKGROUND

Respiratory infection, when getting worse, would lead to complications such as acute kidney injury and pulmonary fibrosis. Complications from such respiratory infection would progress to severe conditions. Once such complications would occur, sequelae would remain even after the respiratory infection cures. For example, in pulmonary fibrosis following respiratory infection, a fibrotic part would remain uncured.

Respiratory infection and subsequent complications rely on different therapeutic policies. If a risk of causing complications following respiratory infection can be determined, a therapeutic policy depending on the risk can be established. Han H. et al. have described in "Profiling serum cytokines in COVID-19 patients reveals IL-6 and IL-10 are disease severity predictors", Emerg Microbes Infect., 2020, vol. 9, pp. 1123-1130 that IL-6 and IL-10 can serve as predictive markers for advanced severity of COVID-19, since measured values of serum IL (interleukin)-6 and IL-10 levels in a severe patient group, among patients with COVID-19 (Coronavirus disease 2019), were found to be significantly higher than in a mild patient group. The document has, however, not described biomarkers for use in determining a risk of causing complications following respiratory infection.

It is therefore an object of the present invention to provide a novel means for acquiring information on respiratory infection, by using a biomarker with which a risk of causing acute kidney injury and pulmonary fibrosis following respiratory infection can be determined.

SUMMARY OF THE INVENTION

The scope of the present invention is defined solely by the appended claims, and is not affected to any degree by the statements within this summary.

The present inventors have found that CXCL9 (CXC chemokine ligand 9), CCL3 (CC chemokine ligand 3), and IL-18 can be used as biomarkers for determining a risk of causing acute kidney injury and pulmonary fibrosis following respiratory infection, and have completed the present invention.

The present invention provides a method for acquiring information on respiratory infection, the method comprising: measuring at least one biomarker in a specimen collected from a subject suffering from a respiratory infection, or from a subject suspected of having the respiratory infection; and determining a risk of causing acute kidney injury or pulmonary fibrosis following respiratory infection, on the basis of a measured value of the biomarker, the biomarker comprising at least one selected from the group consisting of CXCL9, CCL3, and IL-18.

The present invention also provides a method for monitoring a measured value of a biomarker, the method comprising acquiring the measured value of at least one biomarker in each of specimens collected at a plurality of time points from a subject suffering from a respiratory infection, or from a subject suspected of having the respiratory infection, the biomarker comprising at least one selected from the group consisting of CXCL9, CCL3, and IL-18, and a measured value of the biomarker serving as an index of a risk of causing acute kidney injury or pulmonary fibrosis following respiratory infection.

BRIEF DESCRIPTION OF THE DRAWINGS

FIG. 4B is a flowchart illustrating processing procedures with the acquisition device of this embodiment;

FIG. 4C is a flowchart illustrating processing procedures with the acquisition device of this embodiment;

DETAILED DESCRIPTION OF THE PREFERRED EMBODIMENTS

Figure 1A:
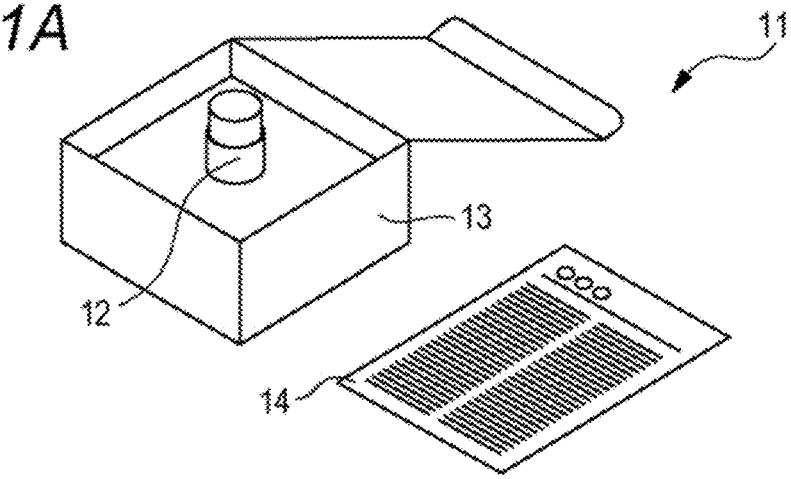
FIG. 1A is a schematic drawing illustrating an exemplary reagent kit of this embodiment.

The method for acquiring information on respiratory infection (hereinafter, also referred to as "acquisition method") according to this embodiment measures at least one biomarker in a specimen collected from a subject suffering from respiratory infection, or from a subject suspected of having respiratory infection.

The respiratory infection refers to diseases triggered by infection of pathogens into respiratory organs such as nasal cavity, pharynx, trachea, bronchi, and alveoli. The pathogen is exemplified by virus, bacteria, fungus, and parasite, although not specifically limited. The virus is exemplified by coronavirus and influenza virus. The coronavirus is exemplified by α-coronavirus, β-coronavirus, γ-coronavirus, and δ-coronavirus, although not specifically limited. β-Coronavirus is exemplified by SARS-CoV-2, SARS-CoV, and MERS-CoV. In a preferred embodiment, the respiratory infection is the one caused by SARS-CoV-2, that is, COVID-19.

The subject is exemplified by patient suffering from respiratory infection and patient suspected of having the respiratory infection. The patient suffering from respiratory infection refers to a person having been confirmed to be infected, typically on the basis of detection of pathogen. The patients preferred as the subject in this embodiment, among the patients having respiratory infection, include patients whose respiratory infection not yet having worsened, patients not yet having caused acute kidney injury following respiratory infection, and patients not yet having caused pulmonary fibrosis following respiratory infection.

A person suspected of having respiratory infection refers to a person possibly having respiratory infection, although the infection remains unconfirmed. Such person is exemplified by a person who has cold symptom such as fever, cough, runny nose, and sore throat and/or symptoms specific to a predetermined respiratory infection including breathlessness, shortness of breath on exertion, and abnormality in taste and smell; a person who has contact with a patient of respiratory infection; and a person suspected of having contact with the patient. The contact with a patient with respiratory infection refers to, for example, a behavior such as talking with the patient at a distance of 1 m or shorter, staying in an ill-ventilated space where the patient resides, or being splashed with saliva, cough or the like of the patient.

The specimen is not particularly limited as long as it is collected from a subject and can contain the aforementioned biomarker. Such samples are exemplified by blood sample, lymph fluid, cerebrospinal fluid, saliva, nasopharyngeal swab, sputum, bronchoalveolar lavage fluid, urine, and feces. The blood sample includes blood (whole blood) collected from the subject, and plasma or serum prepared from the blood. In this embodiment, whole blood, plasma, and serum are preferred, wherein plasma and serum are particularly preferred.

Any insoluble impurity such as cell, if contained in the specimen, may be removed from the specimen by a known technique such as centrifugation or filtration. The specimen may optionally be diluted with an appropriate aqueous medium. Such aqueous medium is not specially limited as long as it does not interfere with measurement of the biomarkers described later, and is exemplified by water, saline and buffer solution. The buffer solution is not specially limited as long as it can demonstrate buffering action at pH around neutral (pH6 or higher and pH8 or lower, for example). Such buffer is exemplified by Good's buffers such as ACES, HEPES, MES and PIPES; phosphate-buffered saline (PBS), Tris hydrochloric acid buffer, and Tris-buffered saline (TBS).

In this embodiment, the biomarker includes one, or two or more protein molecules selected from the group consisting of CXCL9, CCL3, and IL-18. CXCL9, also known as MIG (monokine induced by interferon-γ), is a sort of Th1-type chemokine. CCL3, also known as MIP1a (macrophage inflammatory protein 1 alpha), is a chemokine involved in acute inflammation. IL-18 is a sort of inflammatory cytokine, and induces both Th1 and Th2 responses. These protein molecules per se are known ones, whose amino acid sequences are obtainable, for example, from a known databases such as NCBI (National Center for Biotechnology Information).

In this embodiment, measured values are preferably obtained from two or more biomarkers selected from CXCL9, CCL3, and IL-18. Combinations of the two or more biomarkers are exemplified as below:

combination of CXCL9, with at least one selected from CCL3 and IL-18;
combination of CCL3, with at least one selected from CXCL9 and IL-18;
combination of IL-18, with at least one selected from CXCL9 and CCL3; and
combination of IL-18, CXCL9 and CCL3.

In the present specification, "measuring a biomarker" encompasses acquiring a value that represents the amount or level of the biomarker, and determining a value of the amount or level of the biomarker. The "value that represents the amount or level of the biomarker" depends on the type of labeling substance described later, and can be acquired with use of a measuring instrument suited to the type of labeling substance. Such value is exemplified by measured values of emission intensity, fluorescence intensity, radiation intensity, and optical density. The "value of the amount or level of the biomarker" can be determined on the basis of the value that represents the amount or level of the biomarker, and measured result of a calibrator. The calibrator is a kind of control sample used for quantifying the test substance, which is a sample that contains a known level of the test substance or a corresponding standard substance. In this embodiment, a recombinant protein of each of CXCL9, CCL3, and IL-18, for example, can be used as the calibrator.

In this embodiment, the measured value of the biomarker can be a value that represents the amount or level of the biomarker in the specimen. The measured value of the biomarker can also be a value of the amount or level of the biomarker in the specimen determined on the basis of the measured result of the calibrator.

Means for measuring the biomarker may be suitably selected from known measurement methods, without special limitation. This embodiment prefers a method that includes capturing a biomarker with use of a substance capable of specifically binding to the biomarker. The biomarker contained in the specimen can be measured by detecting the biomarker captured by such substance by a known method.

The substance capable of specifically binding to the biomarker is exemplified by antibody and aptamer. Among them, antibody is particularly preferred. The term "antibody" in this specification encompasses full-length antibody and fragments thereof. The fragments of the antibody are exemplified by reduced IgG (rIgG), Fab, Fab', F(ab')$_2$, Fv, single chain antibody (scFv), diabody and triabody. The antibody may be either monoclonal antibody or polyclonal antibody. Antibodies per se that specifically bind to each of the above biomarkers are known, and widely available. For example, a hybridoma that produces an antibody that specifically binds to a biomarker may be produced by the method described in Kohler G. and Milstein C., Nature, vol. 256, pp. 495-497, 1975, to obtain the antibody. Alternatively, a commercially available antibody may be used.

The method for measuring the biomarker by using the antibody is not particularly limited, and can be appropriately selected from known immunological measurement methods such as enzyme-linked immunosorbent assay (ELISA method), enzyme immunoassay, immunoturbidimetry, immunonephelometry, and latex agglutination. In this embodiment, the ELISA method is preferred. Type of ELISA method may be any of sandwich method, competitive method, direct method, indirect method, or the like, among which the sandwich method is particularly preferred. Paragraphs below will describe an exemplary process of measuring a biomarker in a specimen, by the sandwich ELISA method.

Measurement of the biomarker by the sandwich ELISA method includes forming a complex of an antibody and the biomarker, and detecting the complex. In the forming of a complex, a complex that contains a biomarker, an antibody for capturing the biomarker (also referred to as "capture antibody", hereinafter), and an antibody for detecting the biomarker (also referred to as "detection antibody", hereinafter) is formed on a solid phase. By mixing a specimen with the capture antibody and the detection antibody, the biomarker, if contained in the specimen, can form the complex that contains the biomarker, the capture antibody, and the detection antibody. Then by contacting a solution that contains the complex with the solid phase on which the capture antibody can be immobilized, the complex may be immobilized on the solid phase. Alternatively, the solid phase having the capture antibody preliminarily immobilized thereon may be used. That is, the complex can be formed on the solid phase, by contacting the solid phase having the capture antibody immobilized thereon, the specimen, and the detection antibody. In a case where both of the capture antibody and the detection are monoclonal antibodies, both preferably have different epitopes.

The solid phase may only be an insoluble carrier on which the capture antibody can be immobilized. Mode of immobilization of the capture antibody on the solid phase is not specially limited. For example, the capture antibody and the solid phase may be directly bound, or the capture antibody and the solid phase may be indirectly bound through some other substance. The direct binding is exemplified by physical adsorption. The indirect binding is exemplified by immobilizing a molecule specifically bindable with an antibody on the solid phase, and then immobilizing the antibody on the solid phase, through a bond between the molecule and the antibody. The molecule specifically bindable with the antibody is exemplified by protein A or G, and an antibody that specifically recognizes the antibody (secondary antibody). The capture antibody may alternatively be immobilized on the solid phase, with use of combination of substances interposed between the antibody and the solid phase. Such combination of substances is exemplified by combination of biotins and avidins, and combination of hapten and anti-hapten antibody. The biotins include biotin, and biotin analogs such as desthiobiotin and oxybiotin. The avidins include avidin, and avidin analogs such as streptavidin and Tamavidin (registered trademark). The combination of hapten and anti-hapten antibody is exemplified by combination of a compound having 2,4-dinitrophenyl (DNP) group and an anti-DNP antibody. For example, by using a capture antibody preliminarily modified with any of biotins (or a compound having DNP group), and a solid phase having any of avidins (or anti-DNP antibody) preliminarily immobilized thereon, the capture antibody may be immobilized on the solid phase, through a bond between biotin and avidin (or a bond between DNP group and anti-DNP antibody).

Material for composing the solid phase is selectable, without special limitation, typically from organic polymer compound, inorganic compound, and biopolymer. The organic polymer compound is exemplified by latex, polystyrene and polypropylene. The inorganic compound is exemplified by magnetic substance (iron oxide, chromium oxide, ferrite, etc.), silica, alumina and glass. The biopolymer is exemplified by insoluble agarose, insoluble dextran, gelatin and cellulose. Two or more of them may be used in combination. Shape of the solid phase is exemplified by particle, membrane, microplate, microtube and test tube, without special limitation. Among them, particle is preferred, and magnetic particle is particularly preferred.

In this embodiment, B/F (bound/free) separation for removing any free component that remains unreacted without forming the complex may be interposed between formation of the sandwich immune complex and detection of the complex. The free component that remains unreacted refers to a component that does not constitute a complex. This is exemplified by capture antibody and the detection antibody which remained unbound with the biomarker. Technique for the B/F separation is not specially limited, and may be conducted, in an exemplary case where the solid phase is a particle, by centrifugation so as to collect only the solid phase having the complex bound thereon. With the solid phase given as a container such as a microplate or a microtube, the B/F separation is enabled by removing a liquid that contains the unreacted free component. With the solid phase given as a magnetic particle, the B/F separation is enabled by removing a liquid that contains the unreacted free component under suction through a nozzle, while keeping the magnetic particle magnetically restrained with use of a magnet, which is preferred from the viewpoint of automation. After removing the unreacted free components, the solid phase having the complex bound thereon may be washed with suitable aqueous medium such as PBS.

In the step of detecting the complex, the measured value of the biomarker can be acquired by detecting the complex formed on the solid phase, by a method known in the art. In an exemplary case where an antibody labeled with a labeling substance is used as the detection antibody, the measured value of the biomarker can be acquired by detecting a signal generated by the labeling substance. In an alternative case where a labeled secondary antibody for the detection antibody is used, the measured value of the biomarker can also be acquired in the same manner.

In this embodiment, also an immune complex transfer method described in Japanese Patent Application Laid-Open No. 1-254868 may be used as the as a method for measuring the biomarker with use of antibody.

In this specification, "detecting a signal" encompasses qualitative detection of presence or absence of a signal, quantification of signal intensity, and semi-quantitative detection of signal intensity. The semi-quantitative detection relies upon grade indication of the signal intensity which typically includes "no signal", "weak", "medium" and "strong". In this embodiment, quantitative or semi-quantitative detection of signal intensity is preferred, and quantitative detection of signal intensity is more preferred.

The labeling substance is not specially limited, and may be a substance that can generate a signal by itself (also referred to as "signal generating substance", hereinafter), or may be a substance that catalyzes reaction of some other substance to generate a signal. The signal generating substance is exemplified by fluorescent substance, and radioisotope. The substance that catalyzes reaction of some other substance to generate a detectable signal is exemplified by enzyme. The enzyme is exemplified by alkaline phosphatase, peroxidase, β-galactosidase, and luciferase. The fluorescent substance is exemplified by fluorescent dyes such as fluorescein isothiocyanate (FITC), rhodamine, and Alexa Fluor (registered trademark); and fluorescent protein such as GFP. The radioisotope is exemplified by $^{125}I$, $^{14}C$ and $^{32}P$. The labeling substance is preferably enzyme, among which alkaline phosphatase (ALP) and peroxidase are particularly preferred.

The method for detecting signal per se has been already known in the art. In this embodiment, it suffices to properly select a measurement method suited to the type of signal attributable to the labeling substance. In an exemplary case where the labeling substance is an enzyme, a signal such as light or color, resulted from a reaction of the enzyme with a corresponded substrate, may be measured with use of a known instrument such as a spectrophotometer.

The substrate for the enzyme is properly selectable from known substrates, depending on the type of enzyme. In an exemplary case where alkaline phosphatase is used as the enzyme, the substrate is exemplified by chemiluminescent substrates such as CDP-Star (registered trademark) (disodium 4-chloro-3-(methoxyspiro[1,2-dioxetane-3,2'-(5'-chloro)tricyclo[3.3.1.1 3,7]decane]-4-yl)phenylphosphate), and CSPD (registered trademark) (disodium 3-(4-methoxyspiro[1,2-dioxetane-3,2-(5'-chloro)tricyclo[3.3.1.1 3,7]decane]-4-yl) phenylphosphate); and chromogenic substrate such as 5-bromo-4-chloro-3-indolylphosphate (BCIP), disodium 5-bromo-6-chloro-indolylphosphate, and p-nitrophenyl phosphate. In an exemplary case where peroxidase is used as the enzyme, the substrate is exemplified by chemiluminescent substrates such as luminol and derivatives thereof; and chromogenic substrates such as ammonium 2,2'-azinobis(3-ethylbenzothiazoline-6-sulfonate) (ABTS), 1,2-phenylenediamine (OPD), and 3,3',5,5'-tetramethylbenzidine (TMB).

In a case where the labeling substance is a radioisotope, radiation may be measured as the signal by using a known instrument such as a scintillation counter. In a case where the labeling substance is a fluorescent substance, fluorescence may be measured as the signal by using a known instrument such as a fluorescence microplate reader. Excitation wavelength and fluorescence wavelength may properly be determined depending on the type of fluorescent substance employed.

Results of signal detection may be utilized as the result of measurement of the biomarker. In an exemplary case where signal intensity is detected quantitatively, a measured value of the signal intensity per se, or a value acquired from the measured value may be utilized as the measured value of biomarker. The value acquired from the measured value of the signal intensity is exemplified by a value obtainable by subtracting a measured value of a negative control or a background value, from the measured value. The negative control sample is properly selectable, and is exemplified by buffer free of biomarker, specimen obtained from healthy subject, and specimen obtained from patient with mild or asymptomatic respiratory infection.

In this embodiment, the biomarker contained in a specimen is preferably measured by the sandwich ELISA method that uses the capture antibody immobilized on the magnetic particle and the enzyme-labeled detection antibody. The measurement may be conducted by using a commercially available measuring instrument such as HISCL (registered trademark) Series (manufactured by Sysmex Corporation).

As will be described later in Examples, a patient group having a significantly high measured value of serum CXCL9, CCL3 or IL-18 level was found to include a markedly larger number of patients who developed acute kidney injury or pulmonary fibrosis following respiratory infection, as compared with other patient groups. As described above in this embodiment, the measured result of the biomarker can serve as an index of the risk of causing acute kidney injury or pulmonary fibrosis following respiratory infection. In this embodiment, the risk of causing acute kidney injury or pulmonary fibrosis following respiratory infection means possibility that the subject develops either or both of acute kidney injury and pulmonary fibrosis following respiratory infection, after the elapse of a predetermined period (for example, a day to a month) from the day the specimen was collected from the subject.

In this embodiment, the measured result of the biomarker can be acquired as the information on respiratory infection. The information on respiratory infection is exemplified by information that suggests a high or low risk of causing acute kidney injury and pulmonary fibrosis following respiratory infection, information that suggests a high or low risk of causing acute kidney injury following respiratory infection, and information that suggests a high or low risk of causing pulmonary fibrosis following respiratory infection.

In one embodiment, the acute kidney injury following respiratory infection refers to a rapid decrease in renal function and renal tissue disorder following respiratory infection. The acute kidney injury can be diagnosed typically on the basis of diagnostic criteria according to RIFLE, AKIN or KDIGO. These diagnostic criteria refer to serum creatinine level and urine volume of the subject.

In one embodiment, pulmonary fibrosis following respiratory infection refers to a state in which connective tissue increases in alveolar interstitium damaged by respiratory infection, and a part or whole of the lungs causes sclerosis. The pulmonary fibrosis can be diagnosed typically by chest X-ray examination, chest CT examination, or lung biopsy.

In the pulmonary fibrosis following respiratory infection, the fibrosed part would remain uncured even after the respiratory infection cures, so that the pulmonary fibrosis would remain as a sequela. As will be described later in Examples, some of the patients who showed considerably high measured values of serum CXCL9, CCL3 or IL-18 level, and have suffered from pulmonary fibrosis following respiratory infection were found to retain the pulmonary fibrosis even after judged to be negative regarding pathogen infection. In this embodiment, the measured result of the biomarker can serve as an index of a risk of persistence of pulmonary fibrosis following respiratory infection. That is, information on respiratory infection can suggest a high or low risk of persistence of pulmonary fibrosis following respiratory infection. In this embodiment, the risk of persistence of pulmonary fibrosis following respiratory infection means possibility that a patient, having developed pulmonary fibrosis following respiratory infection, may be found to retain the pulmonary fibrosis, even after judged to be negative regarding pathogen infection. The determination of the pathogen infection may rely upon any of known detection methods suited to the type of pathogen. In an exemplary case where the pathogen is virus, whether the pathogen infection is negative or not is preferably determined by the known PCR method.

In this embodiment, the measured value of a biomarker may be used as an index of the risk of causing acute kidney injury or pulmonary fibrosis following respiratory infection, by comparing the acquired measured value of the biomarker with a predetermined threshold value that corresponds to the biomarker. In one embodiment, the measured value of the biomarker, if found to be equal to or exceeding a predetermined threshold value that corresponds to the biomarker, suggests a high risk of causing acute kidney injury or pulmonary fibrosis following respiratory infection.

In a further embodiment, the measured value of the biomarker, if found to be lower than a predetermined threshold value that corresponds to the biomarker, suggests a low risk of causing acute kidney injury or pulmonary fibrosis following respiratory infection.

In one embodiment where the biomarker includes CXCL9, the measured value of CXCL9, if found to be equal to or exceeding a predetermined threshold value that corresponds to CXCL9, suggests a high risk of causing acute kidney injury or pulmonary fibrosis following respiratory infection. The measured value of CXCL9, if found to be lower than the predetermined threshold value that corresponds to CXCL9, suggests a low risk of causing acute kidney injury or pulmonary fibrosis following respiratory infection.

In one embodiment where the biomarker includes CCL3, the measured value of CCL3, if found to be equal to or exceeding a predetermined threshold value that corresponds to CCL3, suggests a high risk of causing acute kidney injury or pulmonary fibrosis following respiratory infection. The measured value of CCL3, if found to be lower than the predetermined threshold value that corresponds to CCL3, suggests a low risk of causing acute kidney injury or pulmonary fibrosis following respiratory infection.

In one embodiment where the biomarker includes IL-18, the measured value of IL-18, if found to be equal to or exceeding a predetermined threshold value that corresponds to IL-18, suggests a high risk of developing acute kidney injury or pulmonary fibrosis following respiratory infection. The measured value of IL-18, if found to be lower than the predetermined threshold value that corresponds to IL-18, suggests a low risk of causing acute kidney injury or pulmonary fibrosis following respiratory infection.

In a further embodiment, at least two biomarkers in a specimen collected from a subject may be measured. In this embodiment where the biomarker includes at least two selected from the group consisting of CXCL9, CCL3, and IL-18, the measured results of these biomarkers can serve as indices of the risk of causing acute kidney injury or pulmonary fibrosis following respiratory infection. For example, at least one of the acquired measured values of the biomarkers, if found to be equal to or more than a predetermined threshold value that corresponds to the biomarker, suggests a high risk of causing acute kidney injury or pulmonary fibrosis following respiratory infection. The acquired measured values of the biomarkers, if all found to be lower than predetermined threshold values that correspond to the individual biomarkers, suggest a low risk of causing acute kidney injury or pulmonary fibrosis following respiratory infection.

In one embodiment where the biomarker contains two selected from the group consisting of CXCL9, CCL3, and IL-18, at least one of the measured values of the two biomarkers, if found to be equal to or exceeding predetermined threshold values that correspond to the biomarker, suggest a high risk of causing acute kidney injury or pulmonary fibrosis following respiratory infection. In a case where the biomarkers are two selected from the group consisting of CXCL9, CCL3, and IL-18, the measured values of the two biomarkers, if both found to be lower than predetermined threshold values that correspond to the individual biomarkers, suggest a low risk of causing acute kidney injury or pulmonary fibrosis following respiratory infection.

In a further embodiment, at least three biomarkers in a specimen collected from a subject may be measured. In this embodiment where the biomarkers include CXCL9, CCL3, and IL-18, the measured results of these biomarkers can serve as indices of the risk of causing acute kidney injury or pulmonary fibrosis following respiratory infection. For example, at least one of the acquired measured values of the biomarkers, if found to be equal to or more than a predetermined threshold value that corresponds to the biomarker, suggests a high risk of causing acute kidney injury or pulmonary fibrosis following respiratory infection. The acquired measured values of the biomarkers, if all found to be lower than predetermined threshold values that correspond to the individual biomarkers, suggest a low risk of causing acute kidney injury or pulmonary fibrosis following respiratory infection.

In one embodiment where the biomarkers are CXCL9, CCL3 and IL-18, at least one of the measured values of the three biomarkers, if found to be equal to or exceeding a predetermined threshold value that corresponds to the biomarker, suggests a high risk of causing acute kidney injury or pulmonary fibrosis following respiratory infection. In a case where the biomarkers are CXCL9, CCL3, and IL-18, the measured values of the three biomarkers, if all found to be lower than predetermined threshold values that correspond to the individual biomarkers, suggest a low risk of causing acute kidney injury or pulmonary fibrosis following respiratory infection.

In another embodiment, the acquisition method includes measuring at least two biomarkers in a specimen collected from a subject, and the biomarkers include at least two selected from the group consisting of CXCL9, CCL3, and IL-18. On the basis of the measured values of the biomarkers, the risk of causing acute kidney injury or pulmonary fibrosis following respiratory infection is classified into three stages. The stages are specifically as follows:

the acquired measured values of the biomarkers, if all found to be equal to or exceeding predetermined threshold values that correspond to the individual biomarkers, suggest a high risk of causing acute kidney injury or pulmonary fibrosis following respiratory infection;

at least one of the acquired measured values of the biomarkers, if found to be equal to or more than a predetermined threshold value that corresponds to the biomarker, suggests a moderate risk of causing acute kidney injury or pulmonary fibrosis following respiratory infection; and the acquired measured values of the biomarkers, if all found to be lower than predetermined threshold values that correspond to the individual biomarkers, suggest a low risk of causing acute kidney injury or pulmonary fibrosis following respiratory infection.

In one embodiment where the biomarkers are two selected from the group consisting of CXCL9, CCL3, and IL-18, the measured values of the two biomarkers, if both found to be equal to or exceeding predetermined threshold values that correspond to the individual biomarkers, suggest a high risk of causing acute kidney injury or pulmonary fibrosis following respiratory infection. In a case where the biomarkers are two selected from the group consisting of CXCL9, CCL3, and IL-18, at least one of the measured values of the two biomarkers, if found to be equal to or exceeding a predetermined threshold value that corresponds to the biomarker, suggests a moderate risk of causing acute kidney injury or pulmonary fibrosis following respiratory infection. In a case where the biomarkers are two selected from the group consisting of CXCL9, CCL3, and IL-18, the measured values of the two biomarkers, if both found to be lower than predetermined threshold values that correspond to the individual biomarkers, suggest a low risk of causing acute kidney injury or pulmonary fibrosis following respiratory infection.

In one embodiment where the biomarkers are CXCL9, CCL3, and IL-18, the measured values of the three biomarkers, if all found to be equal to or exceeding predetermined threshold values that correspond to the individual biomarkers, suggest a high risk of causing acute kidney injury or pulmonary fibrosis following respiratory infection. In a case where the biomarkers are CXCL9, CCL3, and IL-18, at least one of the measured values of the three biomarkers, if found to be equal to or exceeding a predetermined threshold value that corresponds to the biomarker, suggests a moderate risk of causing acute kidney injury or pulmonary fibrosis following respiratory infection. In a case where the biomarkers are CXCL9, CCL3, and IL-18, the measured values of the three biomarkers, if all found to be lower than predetermined threshold values that correspond to the individual biomarkers, suggest a low risk of causing acute kidney injury or pulmonary fibrosis following respiratory infection.

In this embodiment, other biomarker, besides at least one selected from the group consisting of CXCL9, CCL3, and IL-18, may be measured. Such other biomarker is exemplified by IL-6 and CRP. IL-6 is a type of Th2 type cytokine. CRP is a type of acute phase protein. As will be described later in Examples, a patient group having significantly high measured values of serum IL-6 and CRP levels was found to show a tendency of including a larger number of patients who developed acute kidney injury or pulmonary fibrosis following respiratory infection, as compared with other patient groups. In this embodiment, at least one measured result selected from IL-6 and CRP, and at least one measured result selected from the group consisting of CXCL9, CCL3, and IL-18 may serve as indices of the risk of causing acute kidney injury or pulmonary fibrosis following respiratory infection. Amino acid sequences of IL-6 and CRP per se are known, and are accessible in known databases such as NCBI. IL-6 and CRP can be measured in the same manner as CXCL9, CCL3 and IL-18.

In one embodiment, the biomarker includes at least one selected from the group consisting of CXCL9, CCL3 and IL-18, and at least one selected from the group consisting of IL-6 and CRP. In this embodiment, at least one of the acquired measured values of the biomarkers among CXCL9, CCL3, and IL-18, if found to be equal to or exceeding a predetermined threshold value that corresponds to the biomarker, and, at least one of the acquired measured values of the biomarkers among IL-6 and CRP, if found to be equal to or exceeding a predetermined threshold value that corresponds to the biomarker, suggest a high risk of causing acute kidney injury or pulmonary fibrosis following respiratory infection.

The predetermined threshold values that correspond to the individual biomarkers may be properly set, without special limitation. For example, specimens are collected from a plurality of patients having respiratory infection, and the biomarkers in the specimen are measured to obtain the measured values. After the elapse of a predetermined period (for example, two weeks) from the sample collection, whether or not acute kidney injury or pulmonary fibrosis following respiratory infection has occurred is determined. Data of the acquired measured values are classified into data of a patient group in which acute kidney injury or pulmonary fibrosis developed, and data of a patient group in which acute kidney injury and pulmonary fibrosis did not develop. A value that can most accurately distinguish the two patient groups is then determined for each biomarker, and the value is set as a threshold value. The threshold value can be set while taking sensitivity, specificity, positive predictive value (PPV), negative predictive value (NPV), and so forth into consideration.

In one embodiment, a predetermined threshold value that corresponds to CXCL9 is set typically in the range from 100 pg/mL or above and 365 pg/mL or below. A predetermined threshold value that corresponds to CCL3 is set typically in the range from 47.7 pg/mL or above and 66.7 pg/mL or below. A predetermined threshold value that corresponds to IL-18 is set typically in the range from 600 pg/mL or above and 750 pg/mL or below. A predetermined threshold value that corresponds to IL-6 is set typically in the range from 67.4 pg/mL or above and 96.2 pg/mL or below. A predetermined threshold that corresponds to CRP is set typically in the range from $0.75 \times 10^4$ pg/L or above and $6.2 \times 10^4$ pg/L or below.

A medical worker such as doctor may combine suggestion of the measured value of the biomarker with other information, to determine a risk of causing acute kidney injury or pulmonary fibrosis following respiratory infection. The "other information" includes serum creatinine level, urine volume, finding from X-ray image or CT image of lungs, and other medical findings.

In this embodiment where a subject was suggested to have a high risk of causing acute kidney injury or pulmonary fibrosis following respiratory infection, the subject may be subjected to medical intervention for acute kidney injury or pulmonary fibrosis. The medical interventions include, for example, administration of drugs, dialysis, surgery, immunotherapy, gene therapy, oxygenation therapy, and therapy with a cardiopulmonary bypass. The drug can be properly selected from known therapeutic drugs or candidate drugs for acute kidney injury or pulmonary fibrosis. The medical intervention for acute kidney injury is preferably fluid replacement therapy, renal replacement therapy by dialysis, and anti-inflammatory therapy such as administration of a steroid drug. The medical intervention for pulmonary fibrosis is preferably administration of steroid drug, immunosuppressive drug, anti-fibrotic drug, or the like. The replacement fluid is preferably an isotonic crystalline liquid, which is exemplified by physiological saline and lactated Ringer's solution. The steroid drug is preferably corticosteroid, which is exemplified by dexamethasone and prednisolone. The immunosuppressive drug is exemplified by azathioprine, cyclophosphamide, cyclosporine, and mycophenolate mofetil. Other possible therapies include specific immunotherapy with use of antibody drugs such as anti-IL-6 antibody and anti-IL-1 beta antibody, and immune control/anti-inflammatory therapy with use of biologics such as intravenous immunoglobulin (IVIG). The anti-fibrotic drug is exemplified by pirfenidone, nintedanib, $\alpha v \beta 6$ integrin blocker, Gal-3 inhibitor, autotaxin inhibitor, lysophosphatidic acid inhibitor, JNK inhibitor, mTOR pathway modulator, serum amyloid P component (SAP), and angiotensin 2 receptor (AT2R) inhibitor.

In this embodiment, a temporal change in the measured value of the biomarker in the subject may be acquired as the measured result of the biomarker. The temporal change in the measured value of the biomarker is not particularly limited as long as it is information that represents transition of the measured value of the biomarker in a specimen collected multiple times periodically or non-periodically from a subject. Such temporal change is typically given by a value calculated from a plurality of measured values (difference, ratio, etc. between measured values of two specimens collected at two freely-selected time points), and a record of measured values (table of measured values, graph with plotting of measured values, etc.).

In this embodiment, the measured result of the biomarker is also obtainable by multivariate analysis of the measured values obtained from at least two biomarkers. The value obtainable by multivariate analysis is preferably a predicted value obtainable by multiple logistic regression analysis. Such predicted value may be calculated by a regression equation below.

$$P = 1/[1 + \exp\{-(a_1 x_1 + a_2 x_2 + \ldots + a_n x_n + b)\}]$$

In the regression equation, $x_1$ to $x_n$ represent measured values of the individual biomarkers, $a_1$ to $a_n$ represent regression coefficients of the individual biomarkers, and b represents a constant. The regression coefficients and the constant can be properly determined according to the type of biomarkers to be used. For example, on the basis of measured values of biomarkers in the specimens collected from a plurality of patients (onset group) with the onset of acute kidney injury or pulmonary fibrosis following respiratory infection, and from a plurality of patients (non-onset group) without the onset, the regression coefficient and the constant can be determined by creating a multiple logistic model for discriminating between the onset group and the non-onset group. The multiple logistic model can be created by using statistical analysis software such as SPSS Statistics (from IBM Corporation). In this embodiment, the multiple logistic model is preferably created in advance, from data of the measured values of the biomarkers of respiratory infection patients.

The acquisition method of this embodiment may include determining a risk of causing acute kidney injury or pulmonary fibrosis following respiratory infection, on the basis of the measured value of the biomarkers. In this step, whether the risk of causing acute kidney injury or pulmonary fibrosis following respiratory infection is high or low, may be determined typically on the basis of result of comparison between an acquired measured value of a biomarker, with a threshold values that corresponds to the biomarker. Details of the predetermined threshold are as described above.

In one embodiment, the measured value of the biomarker, if found to be equal to or exceeding a predetermined threshold value that corresponds to the biomarker, can be determined to represent a high risk of causing acute kidney injury or pulmonary fibrosis following respiratory infection. In a further embodiment, the measured value of the biomarker, if found to be lower than a predetermined threshold value that corresponds to the biomarker, may be determined to represent a low risk of causing acute kidney injury or pulmonary fibrosis following respiratory infection.

In one embodiment where the biomarker includes CXCL9, the measured value of CXCL9, if found to be equal to or exceeding a predetermined threshold value that corresponds to CXCL9, may be determined to represent a high risk of causing acute kidney injury or pulmonary fibrosis following respiratory infection. The measured value of CXCL9, if found to be lower than the predetermined threshold value that corresponds to CXCL9, can be determined to represent a low risk of causing acute kidney injury or pulmonary fibrosis following respiratory infection.

In one embodiment where the biomarker includes CCL3, the measured value of CCL3, if found to be equal to or exceeding a predetermined threshold value that corresponds to CCL3, can be determined to represent a high risk of causing acute kidney injury or pulmonary fibrosis following respiratory infection. The measured value of CCL3, if found to be lower than the predetermined threshold value that corresponds to CCL3, can be determined to represent a low risk of causing acute kidney injury or pulmonary fibrosis following respiratory infection.

In one embodiment where the biomarker includes IL-18, the measured value of IL-18, if found to be equal to or exceeding a predetermined threshold value that corresponds to IL-18, may be determined to represent a high risk of developing acute kidney injury or pulmonary fibrosis following respiratory infection. The measured value of IL-18, if found to be lower than the predetermined threshold value that corresponds to IL-18, can be determined to represent a low risk of developing acute kidney injury or pulmonary fibrosis following respiratory infection.

In a further embodiment, at least two biomarkers in a specimen collected from a subject may be measured. In this embodiment where the biomarker include at least two selected from the group consisting of CXCL9, CCL3, and IL-18, the risk of causing acute kidney injury or pulmonary fibrosis following respiratory infection may be determined on the basis of the measured values of these biomarkers. For example, at least one of the acquired measured values of the biomarkers, if found to be equal to or exceeding a predetermined threshold value that corresponds to the biomarker, can be determined to represent a high risk of causing acute kidney injury or pulmonary fibrosis following respiratory infection. The acquired measured values of the biomarkers, if all found to be lower than the predetermined threshold values that correspond to the individual biomarkers, can be determined to represent a low risk of causing acute kidney injury or pulmonary fibrosis following respiratory infection.

In one embodiment where the biomarkers are two selected from the group consisting of CXCL9, CCL3, and IL-18, at least one of the measured values of the two biomarkers, if found to be equal to or exceeding a predetermined threshold value that corresponds to the biomarker, can be determined to represent a high risk of causing acute kidney injury or pulmonary fibrosis following respiratory infection. In a case where the biomarkers are two selected from the group consisting of CXCL9, CCL3, and IL-18, the measured values of the two biomarkers, if both found to be lower than predetermined threshold values that correspond to the individual biomarkers, can be determined to represent a low risk of causing acute kidney injury or pulmonary fibrosis following respiratory infection.

In a further embodiment, at least three biomarkers in a specimen collected from a subject may be measured. In this embodiment where the biomarkers include CXCL9, CCL3, and IL-18, the risk of causing acute kidney injury or pulmonary fibrosis following respiratory infection may be determined on the basis of the measured values of these biomarkers. For example, at least one of the acquired measured values of the biomarkers, if found to be equal to or exceeding a predetermined threshold value that corresponds to the biomarker, can be determined to represent a high risk of causing acute kidney injury or pulmonary fibrosis following respiratory infection. The acquired measured values of the biomarkers, if all found to be lower than the predetermined threshold values that correspond to the individual biomarkers, can be determined to represent a low risk of causing acute kidney injury or pulmonary fibrosis following respiratory infection.

In one embodiment where the biomarkers are CXCL9, CCL3 and IL-18, at least one of the measured values of the three biomarkers, if found to be equal to or exceeding a predetermined threshold value that corresponds to the biomarker, can be determined to represent a high risk of causing acute kidney injury or pulmonary fibrosis following respiratory infection. In a case where the biomarkers are CXCL9, CCL3, and IL-18, the measured values of the three biomarkers, if all found to be lower than predetermined threshold values that correspond to the individual biomarkers, can be determined to represent a low risk of causing acute kidney injury or pulmonary fibrosis following respiratory infection.

In another embodiment where the acquisition method may include measuring at least two biomarkers in a specimen collected from a subject, the biomarkers may include at least two selected from the group consisting of CXCL9, CCL3, and IL-18, and the risk of causing acute kidney injury or pulmonary fibrosis following respiratory infection may be determined in three stages, on the basis of the measured values of these biomarkers. The stages are specifically as follows:

the acquired measured values of the biomarkers, if all found to be equal to or exceeding predetermined threshold values that correspond to the individual biomarkers, can be determined to represent a high risk of causing acute kidney injury or pulmonary fibrosis following respiratory infection;

at least one of the acquired measured values of the biomarker, if found to be equal to or exceeding a predetermined threshold value that corresponds to the biomarker, can be determined to represents a moderate risk of causing acute kidney injury or pulmonary fibrosis following respiratory infection; and the acquired measured values of the biomarkers, if all found to be lower than predetermined threshold values that correspond to the individual biomarkers, can be determined to represent a low risk of causing acute kidney injury or pulmonary fibrosis following respiratory infection.

In one embodiment where the biomarker includes two selected from the group consisting of CXCL9, CCL3, and IL-18, the measured values of the two biomarkers, if both found to be equal to or exceeding predetermined threshold values that correspond to the individual biomarkers, can be determined to represent a high risk of causing acute kidney injury or pulmonary fibrosis following respiratory infection. In a case where the biomarker includes two selected from the group consisting of CXCL9, CCL3, and IL-18, any one of the measured values of the two biomarkers, if found to be equal to or exceeding a predetermined threshold value that corresponds to the biomarker, can be determined to represent a moderate risk of causing acute kidney injury or pulmonary fibrosis following respiratory infection. In a case where the biomarkers are two selected from the group consisting of CXCL9, CCL3, and IL-18, the measured values of the two biomarkers, if both found to be lower than predetermined threshold values that correspond to the individual biomarkers, can be determined to represent a low risk of causing acute kidney injury or pulmonary fibrosis following respiratory infection.

In one embodiment where the biomarkers are CXCL9, CCL3, and IL-18, the measured values of the three biomarkers, if all found to be equal to or exceeding predetermined threshold values that correspond to the individual biomarkers, can be determined to represent a high risk of causing acute kidney injury or pulmonary fibrosis following respiratory infection. In a case where the biomarker includes CXCL9, CCL3, and IL-18, at least one of the measured values of the three biomarkers, if found to be equal to or exceeding a predetermined threshold value that corresponds to the biomarker, can be determined to represent a moderate risk of causing acute kidney injury or pulmonary fibrosis following respiratory infection. In a case where the biomarkers are CXCL9, CCL3, and IL-18, the measured values of the three biomarkers, if all found to be lower than predetermined threshold values that correspond to the individual biomarkers, can be determined to represent a low risk of causing acute kidney injury or pulmonary fibrosis following respiratory infection.

In a further embodiment, the risk of causing acute kidney injury or pulmonary fibrosis following respiratory infection may be determined on the basis of at least one measured value selected from the group consisting of CXCL9, CCL3 and IL-18, and at least one measured value selected from the group consisting of IL-6 and CRP. In this embodiment, at least one of the acquired measured values of the biomarkers among CXCL9, CCL3, and IL-18, if found to be equal to or exceeding a predetermined threshold value that corresponds to the biomarker, and, at least one of the acquired measured values of the biomarkers among IL-6 and CRP, if found to be equal to or exceeding a predetermined threshold value that corresponds to the biomarker, can be determined to represent a high risk of causing acute kidney injury or pulmonary fibrosis following respiratory infection.

In this embodiment, a subject if suggested to have a high risk of causing acute kidney injury or pulmonary fibrosis following respiratory infection may be subjected to medical intervention for acute kidney injury or pulmonary fibrosis.

Hence, one embodiment relates to a therapeutic method for acute kidney injury or pulmonary fibrosis following respiratory infection (also referred to as "therapeutic method", hereinafter). The therapeutic method of this embodiment includes measuring at least one biomarker in a specimen collected from a subject suffering from a respiratory infection, or from a subject suspected of having the respiratory infection; determining a risk of causing acute kidney injury or pulmonary fibrosis following respiratory infection, on the basis of a measured value of the biomarker; and giving medical intervention for acute kidney injury or pulmonary fibrosis to the subject determined to have a high risk, wherein the biomarker including at least one selected from the group consisting of CXCL9, CCL3, and IL-18. Details of the subject, specimen, biomarker and measurement thereof, medical intervention and the like are the same as those described regarding the acquisition method of this embodiment.

In this embodiment, the measured value of the biomarker in the specimen may be monitored. The method for monitoring a measured value of a biomarker of this embodiment (also referred to as "monitoring method", hereinafter) uses specimens collected from a subject at a plurality of time points. At least one biomarker in each specimen is measured, and a measured value of at least one biomarker is acquired from each specimen. Details of the subject, specimen, biomarker, measurement thereof and the like are the same as those described for the acquisition method of this embodiment.

In this embodiment, the plurality of time points may only be two or more different time points. For example, the plurality of time points includes a first time point, and a second time point different from the first time point. The first time point is freely selectable without special limitation. For example, the first time point may be a time point when the subject was found to have developed a respiratory infection, a time point of onset of a symptom of respiratory infection in a subject, a time point when a subject is hospitalized, or the like. The second time point is not particularly limited as long as it is different from the first time point. The second time point is preferably a time point when a period within a month has elapsed from the first time point. The second time point is typically a time point when a period of 0.5 hours, 1 hour, 2 hours, 3 hours, 4 hours, 5 hours, 6 hours, 7 hours, 8 hours, 9 hours, 10 hours, 12 hours, 15 hours, 18 hours, 1 day, 2 days, 3 days, 4 days, 5 days, 6 days, 7 days, 8 days, 9 days, 10 days, 12 days, 2 weeks, 3 weeks, 4 weeks, or 1 month has elapsed from the first time point.

In this embodiment, "specimens collected from a subject at a plurality of time points" means specimens collected from the same subject at each of the plurality of time points. The specimens collected from a subject at a plurality of time points typically includes a first specimen collected from the subject at the first time point, and a second specimen collected from the subject at the second time point different from the first time point. In the monitoring method of this embodiment, the biomarker may be measured every time a specimen is collected, or may collectively be measured after storing the individual collected specimens.

In the monitoring method of this embodiment, the measured value of the biomarker in the same subject is monitored, and the measured value of the biomarker can serve as an index of the risk of causing acute kidney injury or pulmonary fibrosis following respiratory infection. In a preferred embodiment, measured values of the same biomarker are acquired at multiple time points. The acquired measured value of a biomarker may be used as an index of the risk of causing acute kidney injury or pulmonary fibrosis following respiratory infection, by comparing the measured value of the biomarker acquired from each subject with a predetermined threshold value that corresponds to the biomarker. Details of the predetermined threshold value are same as those described previously in relation to the acquisition method of this embodiment.

In one embodiment, the measured value of the biomarker, if found to be equal to or exceeding a predetermined threshold value that corresponds to the biomarker at least at one of the plurality of time points, suggests a high risk of causing acute kidney injury or pulmonary fibrosis following respiratory infection. In a further embodiment, the measured value of the biomarker, if found to be lower than the predetermined threshold value that corresponds to the biomarker at all of the plurality of time points, suggests a low risk of causing acute kidney injury or pulmonary fibrosis following respiratory infection.

In one embodiment where the biomarker includes CXCL9, the measured value of CXCL9, if found to be equal to or exceeding a predetermined threshold value that corresponds to CXCL9 at least at one of the plurality of time points, suggests a high risk of causing acute kidney injury or pulmonary fibrosis following respiratory infection. The measured value of CXCL9, if found to be lower than the predetermined threshold value that corresponds to CXCL9 at all of the plurality of time points, suggests a low risk of causing acute kidney injury or pulmonary fibrosis following respiratory infection.

In one embodiment where the biomarker includes CCL3, the measured value of CCL3, if found to be equal to or exceeding a predetermined threshold value that corresponds to CCL3 at least at one of the plurality of time points, suggests a high risk of causing acute kidney injury or pulmonary fibrosis following respiratory infection. The measured value of CCL3, if found to be lower than the predetermined threshold value that corresponds to CCL3 at all of the plurality of time points, suggests a low risk of causing acute kidney injury or pulmonary fibrosis following respiratory infection.

In one embodiment where the biomarker includes IL-18, the measured value of IL-18, if found to be equal to or exceeding a predetermined threshold value that corresponds to IL-18 at least at one of the plurality of time points, suggests a high risk of causing acute kidney injury or pulmonary fibrosis following respiratory infection. The measured value of IL-18, if found to be lower than the predetermined threshold value that corresponds to IL-18 at all of the plurality of time points, suggests a low risk of causing acute kidney injury or pulmonary fibrosis following respiratory infection.

In a further embodiment, at least two biomarkers in each specimen may be measured. In this embodiment where the biomarker includes at least two selected from the group consisting of CXCL9, CCL3, and IL-18, at least one of the acquired measured values of the biomarkers at least at one time point among a plurality of time points, if found to be equal to or exceeding a predetermined threshold value that corresponds to the biomarker, suggests a high risk of causing acute kidney injury or pulmonary fibrosis following respiratory infection. The measured values of the biomarkers, if all found to be lower than predetermined threshold values that correspond to the biomarkers at all of the plurality of time points, suggest a low risk of causing acute kidney injury or pulmonary fibrosis following respiratory infection.

In one embodiment where the biomarker includes two selected from the group consisting of CXCL9, CCL3, and IL-18, at least one of the measured values of the two biomarkers at least at one time point of the plurality of time points, if found to be equal to or exceeding a predetermined threshold value that corresponds to the biomarker, suggests a high risk of causing acute kidney injury or pulmonary fibrosis following respiratory infection. In a case where the biomarkers are any of two selected from the group consisting of CXCL9, CCL3, and IL-18, the measured values of the two biomarkers, if both found to be lower than predetermined threshold values that correspond to the individual biomarkers at all time points among the plurality of time points, suggest a low risk of causing acute kidney injury or pulmonary fibrosis following respiratory infection.

In a further embodiment, at least three biomarkers in each specimen may be measured. In this embodiment where the biomarker includes CXCL9, CCL3 and IL-18, at least one of the acquired measured values of the biomarkers at least at one of the plurality of time points, if found to be equal to or exceeding a predetermined threshold value that corresponds to the biomarker, suggests a high risk of causing acute kidney injury or pulmonary fibrosis following respiratory infection. The measured values of the biomarkers, if all found to be lower than predetermined threshold values that correspond to the biomarkers at all of the plurality of time points, suggest a low risk of causing acute kidney injury or pulmonary fibrosis following respiratory infection.

In one embodiment where the biomarker includes CXCL9, CCL3 and IL-18, at least one of the measured values of the three biomarkers at least at one time point of the plurality of time points, if found to be equal to or exceeding a predetermined threshold value that corresponds to the biomarker, suggests a high risk of causing acute kidney injury or pulmonary fibrosis following respiratory infection. In a case where the biomarkers include CXCL9, CCL3, and IL-18, the measured values of the three biomarkers, if all found to be lower than predetermined threshold values that correspond to the individual biomarkers at all time points among the plurality of time points, suggest a low risk of causing acute kidney injury or pulmonary fibrosis following respiratory infection.

Conditions for terminating the monitoring method of this embodiment may properly be determined by a medical worker such as doctor, without special limitation. The monitoring method of this embodiment may be terminated, for example, if a high risk of causing acute kidney injury or pulmonary fibrosis following respiratory infection is suggested by the measured values of the biomarker acquired from the specimens collected from the subject at a plurality of time points. In this case, the subject is preferably subjected to medical intervention for acute kidney injury or pulmonary fibrosis. The details of the medical intervention are as described above. The monitoring method of this embodiment may be alternatively terminated, if a low risk of causing acute kidney injury or pulmonary fibrosis following respiratory infection is suggested by the measured values of the biomarker acquired from the specimens collected from the subject at a plurality of time points, and, if no sign of acute kidney injury or pulmonary fibrosis is found in the subject.

Having described in the embodiments that the measured value of a biomarker, if found to be equal to a predetermined threshold value that corresponds to the biomarker, may suggest or may be determined to represent a high risk of causing acute kidney injury or pulmonary fibrosis following respiratory infection, the measured value may suggest, or may be determined to represent a low risk.

One embodiment relates to a reagent kit for use in the aforementioned acquisition method, monitoring method, or therapeutic method of this embodiment. The reagent kit of this embodiment contains at least one selected from the group consisting of a reagent that contains a substance capable of specifically binding to CXCL9, a reagent that contains a substance capable of specifically binding to CCL3, and a reagent that contains a substance capable of specifically binding to IL-18. In a further embodiment, the reagent kit may further include at least one selected from the group consisting of a reagent that contains a substance capable of specifically binding to IL-6, and a reagent that contains a substance capable of specifically binding to CRP. The substance capable of specifically binding to each biomarker is exemplified by antibody and aptamer. Among them, antibody is preferred.

The reagent kit of this embodiment may be provided with the individual reagents filled in vials and packaged in a box. The box may include a package insert. The package insert may contain descriptions on contents of the reagent kit, compositions of the individual reagents, instructions for use, and so forth. An example of the reagent kit of this embodiment is illustrated in FIG. 1A. In FIG. 1A, reference numeral 11 denotes a reagent kit, reference numeral 12 denotes a vial filled with a reagent that contains a substance capable of specifically binding to CXCL9, reference numeral 13 denotes a packaging box, and reference numeral 14 denotes a package insert. In place of the reagent that contains the substance capable of specifically binding to CXCL9, the reagent kit of this example may alternatively contain a reagent that contains a substance capable of specifically binding to CCL3, or a reagent that contains a substance capable of specifically binding to IL-18. The package insert in this case will have descriptions on a reagent composition, a method of use and the like, for the reagent that contains a substance capable of specifically binding to CCL3, or for the reagent that contains a substance capable of specifically binding to IL-18. The reagent kit may further contain a reagent that contains a substance capable of specifically binding to CCL3, or a reagent that contains a substance capable of specifically binding to IL-18, in addition to the reagent that contains the substance capable of specifically binding to CXCL9. The package insert in this case will have descriptions on reagent compositions, a method of use and the like, for a reagent that contains a substance capable of specifically binding to CXCL9, as well as for the reagent that contains the substance capable of specifically binding to CCL3, or for the reagent that contains the substance capable of specifically binding to IL-18. The reagent kit may also contain the reagent that contains the substance capable of specifically binding to CXCL9, the reagent that contains the substance capable of specifically binding to CCL3, and the reagent that contains the substance capable of specifically binding to IL-18. The package insert in this case will have descriptions on the reagent compositions, a method of use and the like, for the reagent that contains the substance capable of specifically binding to CXCL9, for the reagent that contains the substance capable of specifically binding to CCL3, and for the reagent that contains the substance capable of specifically binding to IL-18.

In a preferred embodiment, the reagent kit of this embodiment contains the capture antibody and the detection antibody. The detection antibody may be labeled with a labeling substance. Details of the capture antibody, the detection antibody, and the labeling substance are the same as those described previously in relation to the acquisition method of this embodiment. The reagent kit may contain a solid phase.

In a case where the labeling substance used for the detection antibody is an enzyme, the reagent kit may contain a substrate for the enzyme. Details of the solid phase and the substrate are the same as those described previously in relation to the acquisition method of this embodiment.

Figure 1B:
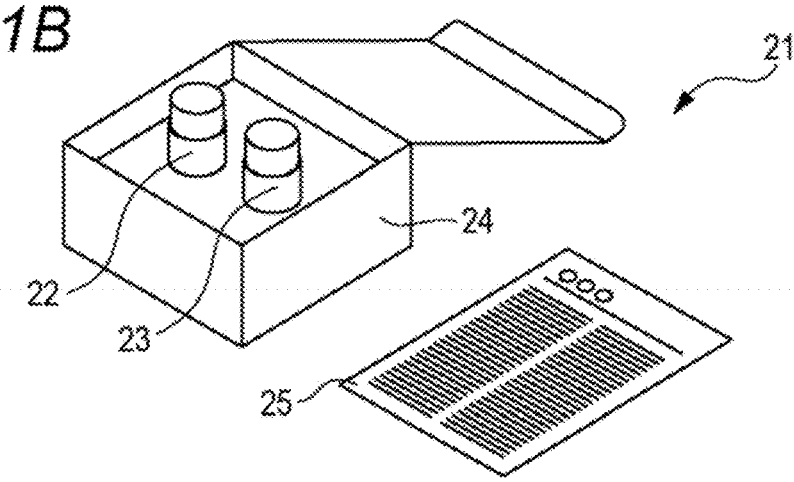
FIG. 1B is a schematic drawing illustrating an exemplary reagent kit of this embodiment.

An exemplary reagent kit of further embodiment is illustrated in FIG. 1B. In FIG. 1B, reference numeral 21 denotes a reagent kit, reference numeral 22 denotes a first vial filled with a reagent that contains capture antibody for CXCL9, reference numeral 23 denotes a second vial filled with a reagent that contains a labeled detection antibody for CXCL9, reference numeral 24 denotes a packaging box, and reference numeral 25 denotes a package insert. The reagent kit of this example may contain reagents that individually contain the capture antibody and the labeled detection antibody for CCL3, or reagents that individually contain the capture antibody and the labeled detection antibody for IL-18, in place of the reagents that individually contain the capture antibody and the labeled detection antibody for CXCL9. The reagent kit may further contain the reagents that individually contain the capture antibody and the labeled detection antibody for CCL3, and/or the reagents that individually contain the capture antibody and the labeled detection antibody for IL-18, in addition to the reagents that individually contain the capture antibody and the labeled detection antibody for CXCL9.

Any of the reagent kits described above preferably includes a calibrator. The calibrator is exemplified by calibrator for quantifying CXCL9 (calibrator for CXCL9), calibrator for quantifying CCL3 (calibrator for CCL3), and calibrator for quantifying IL-18 (calibrator for IL-18). The calibrator for CXCL9 may include, for example, a buffer free of CXCL9 (negative control), and a buffer that contains a known concentration of CXCL9. The calibrator for CCL3 may include, for example, a buffer free of CCL3 (negative control), and a buffer that contains a known concentration of CCL3. The calibrator for IL-18 may include, for example, a buffer free of IL-18 (negative control), and a buffer that contains a known concentration of IL-18.

Figure 1C:
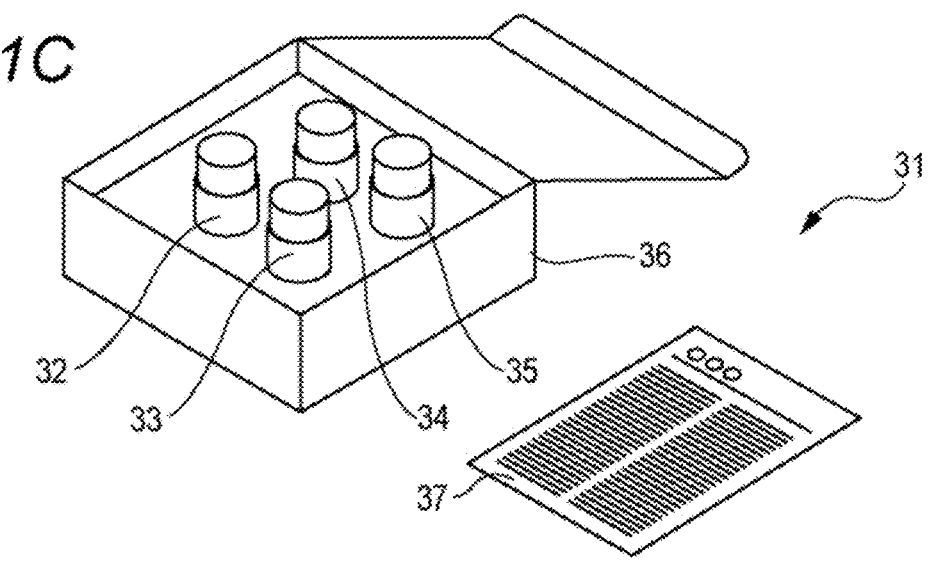
FIG. 1C is a schematic drawing illustrating an exemplary reagent kit of this embodiment.

An exemplary reagent kit of further embodiment is illustrated in FIG. 1C. In FIG. 1C, reference numeral 31 denotes a reagent kit, reference numeral 32 denotes a first vial filled with a reagent that contains a capture antibody for CXCL9, reference numeral 33 denotes a second vial filled with a reagent that contains a labeled detection antibody for CXCL9, reference numeral 34 denotes a third vial filled with a buffer solution free of CXCL9, reference numeral 35 denotes a fourth vial filled with a buffer solution that contains a predetermined concentration of CXCL9, reference numeral 36 denotes a packaging box, and reference numeral 37 denotes a package insert. Each of the buffer solution free of CXCL9 and the buffer solution that contains a predetermined concentration of CXCL9 can be used as a calibrator for CXCL9. The reagent kit of this example may include reagents that individually contain the capture antibody and the labeled detection antibody for CCL3 as well as a calibrator for CCL3, or, reagents that individually contain the capture antibody and the labeled detection antibody for IL-18 as well as a calibrator for IL-18, in place of the reagents that individually contain the capture antibody and the labeled detection antibody for CXCL9 as well as the calibrator for CXCL9. The reagent kit may further contain the reagents that individually contain the capture antibody and the labeled detection antibody for CCL3 as well as the calibrator for CCL3, and/or, the reagents that contain the capture antibody and the labeled detection antibody for IL-18 as well as the calibrator for IL-18, in addition to the reagents that individually contain the capture antibody and the labeled detection antibody for CXCL9 as well as the calibrator for CXCL9.

One embodiment relates to use of a reagent that contains a substance capable of specifically binding to a biomarker, for manufacture of the aforementioned reagent kit. This embodiment relates to use of a reagent for manufacturing a reagent kit used for acquiring information on respiratory infection, in which the reagent contains at least one selected from the group consisting of a reagent that contains a substance capable of specifically binding to CXCL9, a reagent that contains a substance capable of specifically binding to CCL3, and a reagent that contains a substance capable of specifically binding to IL-18.

A further embodiment relates to use of a reagent for manufacturing a reagent kit used for monitoring a measured value of a biomarker, in which the reagent contains at least one selected from the group consisting of a reagent that contains a substance capable of specifically binding to CXCL9, a reagent that contains a substance capable of specifically binding to CCL3, and a reagent that contains a substance capable of specifically binding to IL-18.

One embodiment relates to a device for acquiring information on respiratory infection, and a computer program product for acquiring information on respiratory infection. A further embodiment relates to a device for monitoring the measured value of the biomarker, and a computer program product for monitoring the measured value of the biomarker.

An exemplary acquisition device of this embodiment will be described referring to a drawing. Note, however, this embodiment is not limited solely to an embodiment illustrated in this example. An acquisition device 10 illustrated in FIG. 2 includes an immunoassay device 20, and a computer system 30 that is connected to the immunoassay device 20. The monitoring device of this embodiment may have the same configuration as the acquisition device of this embodiment.

The type of the immunoassay device is properly selectable depending on the measurement method of biomarker, without special limitation. The immunoassay device, in a case where the biomarker is measured by the ELISA method, is not particularly limited as long as it can detect a signal ascribed to the labeling substance employed. In the example illustrated in FIG. 2, the immunoassay device 20 is a commercially available automated immunoassay device capable of detecting a chemiluminescent signal generated in the sandwich ELISA method that uses a magnetic particle having a capture antibody immobilized thereon, and an enzyme-labeled detection antibody.

Upon setting of a reagent that contains magnetic particles having a capture antibody immobilized thereon, a reagent that contains an enzyme-labeled detection antibody, and a specimen collected from a subject on the immunoassay device 20, the immunoassay device 20 carries out an antigen-antibody reaction with use of the individual reagents, acquires a chemiluminescent signal as optical information ascribed to the enzyme-labeled antibody specifically bound to the biomarker, and transmits the obtained optical information to the computer system 30.

Figure 2:
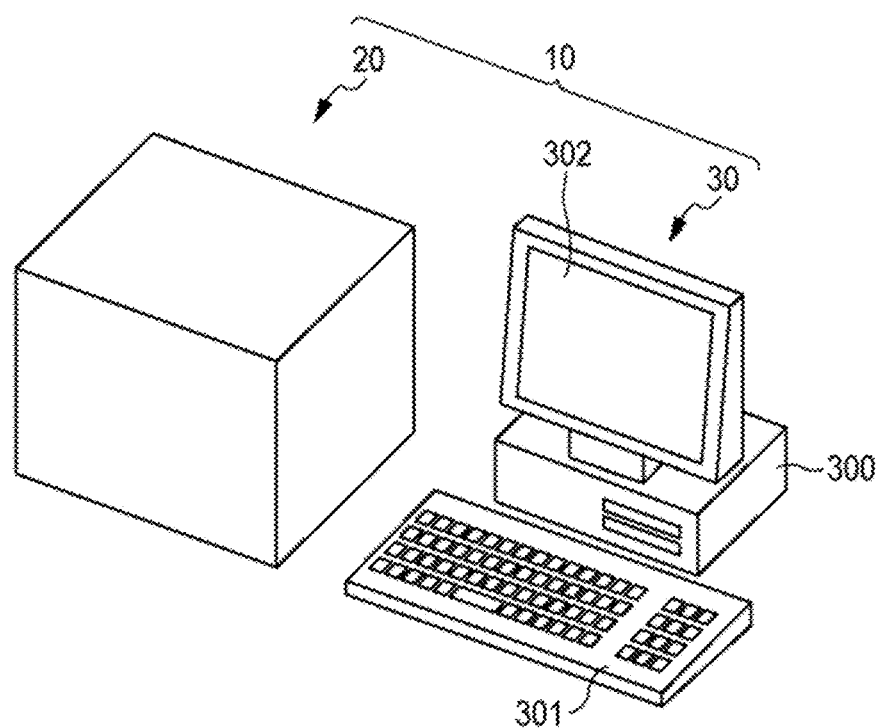
FIG. 2 is a schematic drawing illustrating an exemplary acquisition device according to this embodiment.

Referring now to FIG. 2, the computer system 30 includes a computer main body 300, an input unit 301, and a display unit 302 that displays specimen information, results of determination and the like. The computer system 30 receives the optical information from the immunoassay device 20. A processor of the computer system 30 then runs a computer program product installed in solid state drive (hereinafter, referred to as "SSD") 313, to acquire information on respiratory infection on the basis of the optical information. The computer system 30 may be a device independent from the immunoassay device 20 as illustrated in FIG. 2, or may be a device that incorporates the immunoassay device 20. In the latter case, the computer system 30 per se may constitute the acquisition device 10. The computer program product for acquiring information on respiratory infection may alternatively be installed on a commercially available automated immunoassay device. The acquisition device 10 may be a device having the immunoassay device 20 and the computer system 30 integrated therein.

Figure 3:
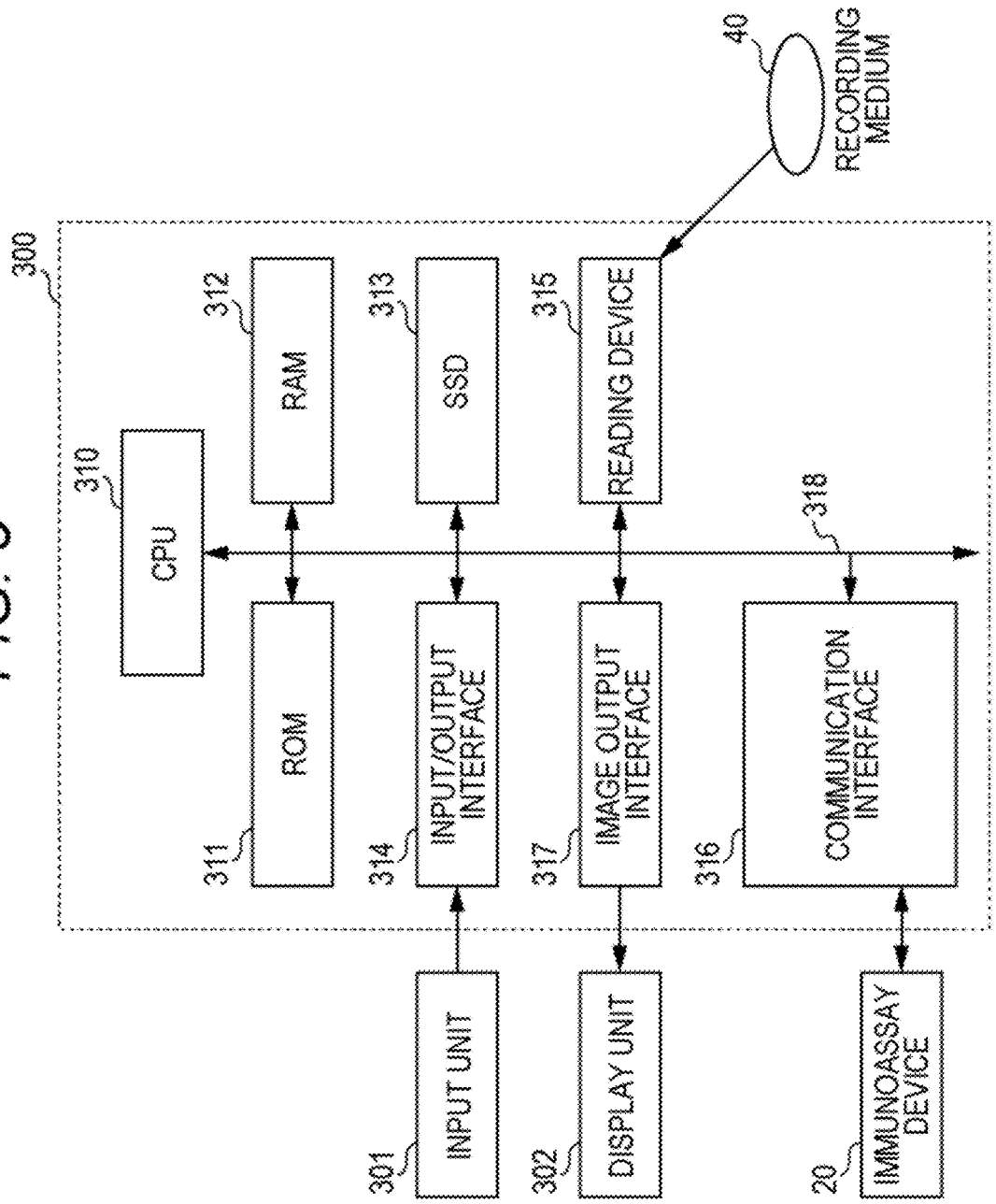
FIG. 3 is a block diagram illustrating a hardware configuration of the acquisition device of this embodiment.

Referring now to FIG. 3, the computer main body 300 has a central processing unit (CPU) 310, a read only memory (ROM) 311, a random access memory (RAM) 312, the SSD 313, an input/output interface 314, a reading device 315, a communication interface 316, and an image output interface 317. The CPU 310, the ROM 311, the RAM 312, the SSD 313, the input/output interface 314, the reading device 315, the communication interface 316, and the image output interface 317 are data-communicably connected through a bus 318. The immunoassay device 20 is communicably connected to the computer system 30 through a communication interface 316.

The CPU 310 can run a program product stored in the ROM 311 or the SSD 313, and a program product loaded on the RAM 312. The CPU 310 calculates a measured value of a biomarker, and displays the measured value on the display unit 302.

The ROM 311 is constituted by a mask ROM, a PROM, an EPROM, an EEPROM or the like. The ROM 311 has stored therein a computer program product executed by the CPU 310 as described above, and data used for running of the computer program product. The computer program product recorded in the ROM 311 contains a basic input output system (BIOS). The predetermined threshold values for the individual biomarkers may preliminarily be stored in the ROM 311 or the SSD 313 when the computer system is manufactured, or may be stored in the ROM 311 or the SSD 313 upon entering through the input unit 301.

The RAM 312 is constituted by an SRAM, a DRAM or the like. The RAM 312 is used for reading program products recorded in the ROM 311 and the SSD 313. The RAM 312 is also used as a working area of the CPU 310 when these programs are run.

The SSD 313 has installed therein an operating system to be run by the CPU 310, a computer program product such as an application program product, and data used for running the computer program product. A hard disk drive may be used in place of the SSD.

The reading device 315 is constituted by a flexible disk drive, a CD-ROM drive, a DVD-ROM drive, a USB port, an SD card reader, a CF card reader, a memory stick reader, or the like. The reading device 315 can read a program product or data recorded in a portable recording medium 40 that corresponds to the aforementioned reading device 315.

The input/output interface 314 is typically constituted by a serial interface such as USB or IEEE 1394, and an analog interface that includes a D/A converter, an A/D converter and so forth. An input unit 301 such as a keyboard and a mouse is connected to the input/output interface 314. The operator can enter various commands through the input unit 301 to the computer main body 300.

The communication interface 316 is typically a wireless interface that conforms to a standard such as an Ethernet (registered trademark) interface. The computer main body 300 can also transmit print data through the communication interface 316, to a printer or the like. In a case where the communication interface 316 is a wireless interface, the computer main body 300 can transmit data to a mobile device such as mobile phone or tablet terminal.

The image output interface 317 conforms to a standard such as D-Sub, DVI-I, DVI-D, HDMI (registered trademark), or DisplayPort. The image output interface 317 is connected through a cable that conforms to the standard, to a display unit 302 that is constituted by an LCD, a CRT or the like. Hence, the display unit 302 can output a video signal that corresponds to the image data received from the CPU 310. The display unit 302 displays an image (screen) in response to the input video signal.

Figure 4A:
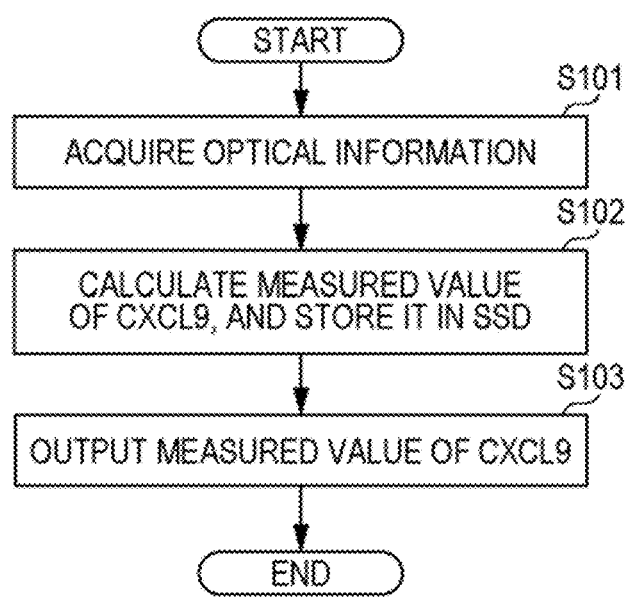
FIG. 4A is a flowchart illustrating processing procedures with the acquisition device of this embodiment.

A processing procedure run on the acquisition device 10 of this embodiment will be described, referring to the drawings. A processing procedure in a case where a measured value of one biomarker is acquired and output will be described, referring to FIG. 4A. In this example, a measured value of CXCL9 is acquired from a chemiluminescent signal that generates in the sandwich ELISA method that uses a magnetic particles having a capture antibody immobilized thereon, and an enzyme-labeled detection antibody, and then output. Alternatively a measured value of CCL3 or IL-18 may be acquired, in place of the measured value of CXCL9.

In step S101, the CPU 310 acquires optical information (chemiluminescent signal) from the immunoassay device 20. In step S102, the CPU 310 calculates the measured value of CXCL9 from the acquired optical information, and acquires the measured value of CXCL9 as the measured result. The CPU 310 stores the measured value in the SSD 313. In step S103, the CPU 310 outputs the measured value of the CXCL9. For example, the CPU 310 handles the measured value of the CXCL9, so as to display it on the display unit 302, print it with the printer, or transmit it to the mobile device. When outputting the measured value of CXCL9, also a predetermined threshold value that corresponds to CXCL9 may be output as reference information.

Hence, the acquisition device of this embodiment can provide a doctor and so forth with the measured value of the biomarker as the information on respiratory infection. As described above, the measured value of the biomarker can serve as an index of a risk of causing acute kidney injury or pulmonary fibrosis following respiratory infection.

In a further embodiment, the measured values of two biomarkers are acquired and output. For example, when acquiring and outputting the measured values of CXCL9 and CCL3, the CPU 310 acquires optical information (chemiluminescent signal) from the immunoassay device 20, calculates the measured values of CXCL9 and CCL3 from the acquired optical information, and stores the measured values in the SSD 313. The CPU 310 outputs the measured values of CXCL9 and CCL3. For example, the CPU 310 handles the measured values of CXCL9 and CCL3, so as to display them on the display unit 302, print them with the printer, or transmit them to the mobile device. When outputting the measured values of CXCL9 and CCL3, also predetermined threshold values that individually correspond to CXCL9 and CCL3 may be output as reference information. The measured value of IL-18 may alternatively be acquired, in place of the measured value of CXCL9 or CCL3.

In a further embodiment, the measured values of CXCL9, CCL3, and IL-18 are acquired and output. In this case, the CPU 310 acquires optical information (chemiluminescent signal) from the immunoassay device 20, calculates the measured values of CXCL9, CCL3, and IL-18 from the acquired optical information, and stores the measured values in the SSD 313. The CPU 310 outputs the measured values of CXCL9, CCL3, and IL-18. For example, the CPU 310 handles the measured values of CXCL9, CCL3, and IL-18, so as to display them on the display unit 302, print them with the printer, or transmit them to the mobile device. When outputting the measured values of CXCL9, CCL3, and IL-18, also predetermined threshold values that individually correspond to CXCL9, CCL3, and IL-18 may be output as reference information.

A process flow in a case where the risk of causing acute kidney injury or pulmonary fibrosis following respiratory infection is determined on the basis of the measured value of one biomarker, will be explained referring to FIG. 4B. In step S201, the CPU 310 acquires optical information (chemiluminescent signal) from the immunoassay device 20. In step S202, the CPU 310 calculates the measured value of CXCL9 from the acquired optical information, and acquires the measured value of CXCL9 as the measured result. The CPU 310 stores the measured value in the SSD 313. In step S203, the CPU 310 compares the calculated measured value of CXCL9 with a predetermined threshold value that corresponds to CXCL9, having been stored in the SSD 313. If the measured value of CXCL9 is found to be equal to or exceeding the threshold value, the process advances to step S204. In step S204, the CPU 310 stores the determination result that represents a high risk of causing acute kidney injury or pulmonary fibrosis, in the SSD 313. If the measured value of CXCL9 is found to be lower than the threshold value in step S203, the process advances to step S205. In step S205, the CPU 310 stores the determination result that represents a low risk of causing acute kidney injury or pulmonary fibrosis, in the SSD 313. In step S206, the CPU 310 outputs the determination result. For example, the CPU 310 handles the determination result, so as to display it on the display unit 302, print it with the printer, or transmit it to the mobile device. In this example, the measured value of CCL3 or IL-18 may alternatively be acquired, in place of the measured value of CXCL9. As described above, the acquisition device of this embodiment can provide a doctor or the like with a determination result of the risk of causing acute kidney injury or pulmonary fibrosis following respiratory infection, as the information on respiratory infection.

Hereinafter, the predetermined threshold value that corresponds to CXCL9 is referred to as a "first threshold value", the predetermined threshold value that corresponds to CCL3 is referred to as a "second threshold value", and the predetermined threshold value that corresponds to IL-18 is referred to as a "third threshold value".

A process flow in a case where the risk of causing acute kidney injury or pulmonary fibrosis following respiratory infection is determined on the basis of the measured values of two biomarkers, will be explained referring to FIG. 4C. In step S301, the CPU 310 acquires optical information (chemiluminescent signal) from the immunoassay device 20. In step S302, the CPU 310 calculates the measured values of CXCL9 and CCL3 from the acquired optical information, and acquires the measured values of CXCL9 and CCL3 as measured results. The CPU 310 stores the measured value in the SSD 313. In step S303, the CPU 310 compares the calculated measured value of CXCL9 with the first threshold value having been stored in the SSD 313. If the measured value of CXCL9 is found to be lower than the first threshold value, the process advances to step S304. In step S304, the calculated measured value of CCL3 is compared with the second threshold value having been stored in the SSD 313. If the measured value of CCL3 is found to be lower than the second threshold value, the process advances to step S305. In step S305, the CPU 310 stores the determination result that represents a low risk of causing acute kidney injury or pulmonary fibrosis, in the SSD 313.

If the measured value of CXCL9 is found to be equal to or exceeding the first threshold value in step S303, the process advances to step S306. If the measured value of CCL3 is found to be equal to or exceeding the second threshold value in step S304, the process advances to step S306. In step S306, the CPU 310 stores the determination result that represents a high risk of causing acute kidney injury or pulmonary fibrosis, in the SSD 313. In step S307, the CPU 310 outputs the determination result. For example, the CPU 310 handles the determination result, so as to display it on the display unit 302, print it with the printer, or transmit it to the mobile device. In this example, the processing order of S303 and S304 may be changed. In this example, the measured value of IL-18 may alternatively be acquired, in place of the measured value of CXCL9 or CCL3. When acquiring the measured value of IL-18, the CPU 310 compares the measured value of IL-18 with the third threshold value.

In another embodiment, the acquisition device may determine a high risk of acute kidney injury or pulmonary fibrosis following respiratory infection, if both of the measured values of the two biomarkers are found to be equal to or exceeding the predetermined threshold values that correspond to the individual biomarkers. The flow in this case will be explained. The CPU 310 acquires optical information (chemiluminescent signal) from the immunoassay device 20, calculates measured values of CXCL9 and CCL3 from the acquired optical information, and stores the measured values in the SSD 313. The CPU 310 compares the measured value of CXCL9 with the first threshold value. If the measured value of CXCL9 is found to be equal to or exceeding the first threshold value, the CPU 310 compares the measured value of CCL3 with the second threshold value. If the measured value of CCL3 is found to be equal to or exceeding the second threshold value, the CPU 310 stores the determination result that represents a high risk of causing acute kidney injury or pulmonary fibrosis, in the SSD 313. If the measured value of CXCL9 is found to be lower than the first threshold value, or, if the measured value of CCL3 is found to be lower than the second threshold value, the CPU 310 stores the determination result that represents a low risk of causing acute kidney injury or pulmonary fibrosis, in the SSD 313. The CPU 310 outputs the determination result. For example, the CPU 310 handles the determination result, so as to display it on the display unit 302, print it with the printer, or transmit it to the mobile device. In this example, the measured value of IL-18 may alternatively be acquired, in place of the measured value of CXCL9 or CCL3. When acquiring the measured value of IL-18, the CPU 310 compares the measured value of IL-18 with the third threshold value.

Figure 4D:
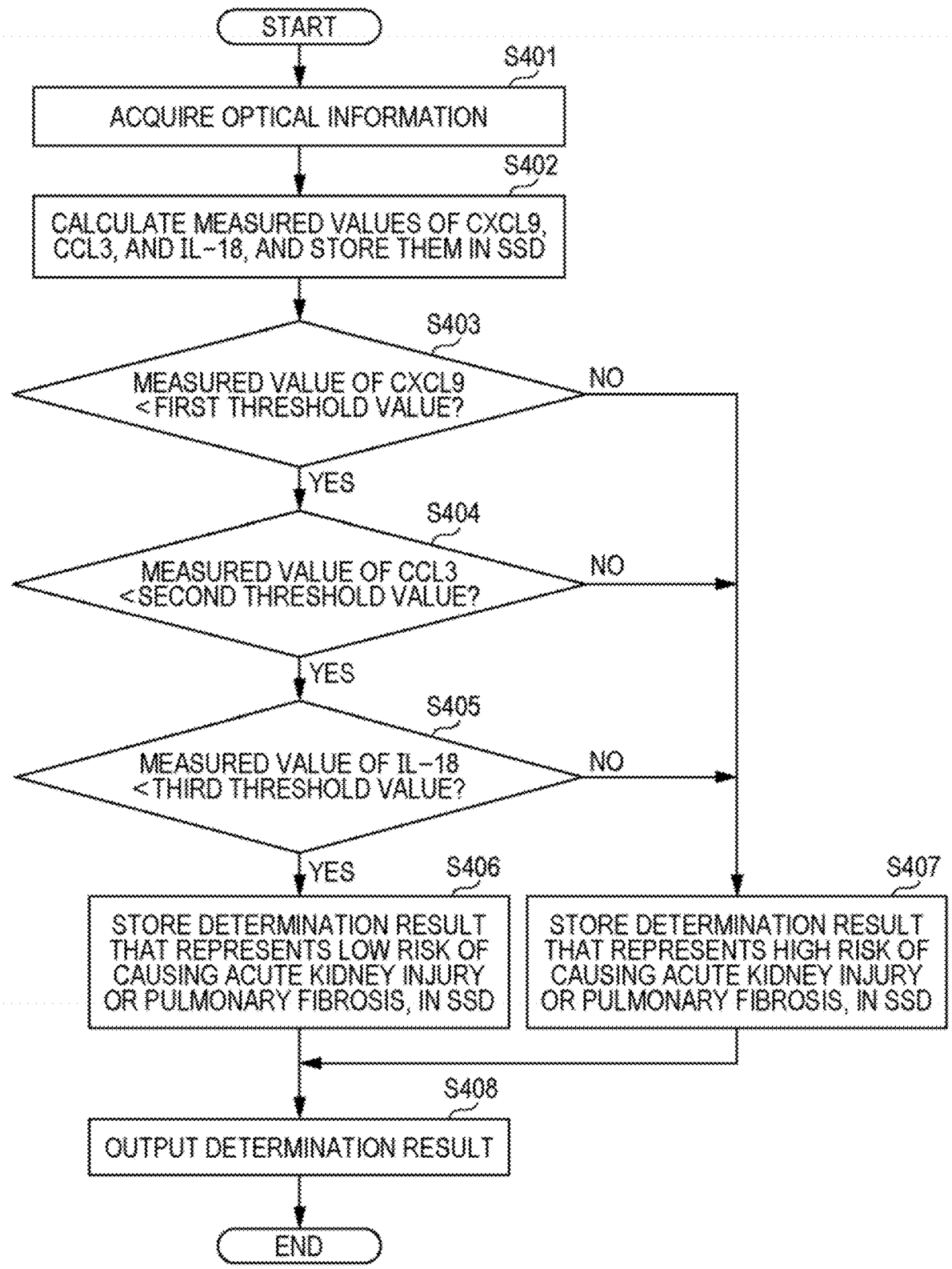
FIG. 4D is a flowchart illustrating processing procedures with the acquisition device of this embodiment.

A process flow in the case where the risk of causing acute kidney injury or pulmonary fibrosis following respiratory infection is determined on the basis of the measured values of CXCL9, CCL3, and IL-18 will be explained, referring to FIG. 4D. In step S401, the CPU 310 acquires optical information (chemiluminescent signal) from the immunoassay device 20. In step S402, the CPU 310 calculates the measured values of CXCL9, CCL3, and IL-18 from the acquired optical information, and acquires the measured values of CXCL9, CCL3, and IL-18 as the measured results. The CPU 310 stores the measured value in the SSD 313. In step S403, the CPU 310 compares the calculated measured value of CXCL9 with the first threshold value having been stored in the SSD 313. If the measured value of CXCL9 is found to be lower than the first threshold value, the process advances to step S404. In step S404, the calculated measured value of CCL3 is compared with the second threshold value having been stored in the SSD 313. If the measured value of CCL3 is found to be lower than the second threshold value, the process advances to step S405. In step S405, the calculated measured value of IL-18 is compared with the third threshold value having been stored in the SSD 313. If the measured value of IL-18 is found to be lower than the third threshold value, the process advances to step S406. In step S406, the CPU 310 stores the determination result that represents a low risk of causing acute kidney injury or pulmonary fibrosis, in the SSD 313.

If the measured value of CXCL9 is found to be equal to or exceeding the first threshold value in step S403, the process advances to step S407. If the measured value of CCL3 is found to be equal to or exceeding the second threshold value in step S404, the process advances to step S407. If the measured value of IL-18 is found to be equal to or exceeding the third threshold value in step S405, the process advances to step S407. In step S407, the CPU 310 stores the determination result that represents a high risk of causing acute kidney injury or pulmonary fibrosis, in the SSD 313. In step S408, the CPU 310 outputs the determination result. For example, the CPU 310 handles the determination result, so as to display it on the display unit 302, print it with the printer, or transmit it to the mobile device. In this example, the processing order of step S403, step S404, and step S405 may be changed.

In another embodiment, the acquisition device may determine a high risk of causing acute kidney injury or pulmonary fibrosis following respiratory infection, when all of the measured values of CXCL9, CCL3, and IL-18 are found to be equal to or exceeding predetermined threshold values that correspond to the individual biomarkers. The flow in this case will be explained. The CPU 310 acquires optical information (chemiluminescent signal) from the immunoassay device 20, calculates measured values of CXCL9, CCL3, and IL-18 from the acquired optical information, and stores the measured values in the SSD 313. The CPU 310 compares the measured value of CXCL9 with the first threshold value. If the measured value of CXCL9 is found to be equal to or exceeding the first threshold value, the CPU 310 compares the measured value of CCL3 with the second threshold value. If the measured value of CCL3 is found to be equal to or exceeding the second threshold value, the CPU 310 compares the measured value of IL-18 with the third threshold value. If the measured value of IL-18 is found to be equal to or more than the third threshold value, the CPU 310 stores the determination result that represents a high risk of causing acute kidney injury or pulmonary fibrosis, in the SSD 313. If the measured value of CXCL9 is found to be lower than the first threshold value, if the measured value of CCL3 is found to be lower than the second threshold value, or if the measured value of IL-18 is found to be lower than the third threshold value, the CPU 310 stores the determination result that represents a low risk of causing acute kidney injury or pulmonary fibrosis, in the SSD 313. The CPU 310 outputs the determination result. For example, the CPU 310 handles the determination result, so as to display it on the display unit 302, print it with the printer, or transmit it to the mobile device.

Hereinafter, the present disclosure will be further detailed referring to Examples, to which the disclosure is by no means limited. Hereinafter, "HISCL" is a registered trademark of Sysmex Corporation.

EXAMPLES

Example 1

Biomarkers with which patients having high risk of causing acute kidney injury or pulmonary fibrosis following respiratory infection are discriminable were identified, by using specimens collected from patients with respiratory infection. The measured values of the biomarkers of the patients with respiratory infection were monitored during the period of hospital admission.

(1) Subject and Specimen

The subjects were fifty-six COVID-19 patients whose infection with SARS-CoV-2 was confirmed by PCR test, and who were hospitalized in Kobe City Medical Center General Hospital. Blood was sampled from each subject within 3 days from the day of hospital admission. Thereafter, blood was sampled from each subject at multiple time points. The sampled blood was used as a specimen. Whether each patient has developed acute kidney injury or not was diagnosed according to the diagnostic criteria of KDIGO. Whether pulmonary fibrosis has occurred or not was diagnosed by chest CT examination. Sixteen subjects were determined to cause acute kidney injury during the hospital admission. Among them, eight subjects had already developed acute kidney injury on the day of hospital admission, and the other eight subjects developed acute kidney injury after the day of the first blood sampling. Twenty-eight subjects were found to cause pulmonary fibrosis during the hospital admission. Among them, fourteen patients were found to retain pulmonary fibrosis even after judged by the PCR test to be negative regarding SARS-CoV-2 infection, and the other fourteen patients were found to retain no pulmonary fibrosis. Each of the population of subjects with acute kidney injury, and the population of subjects with pulmonary fibrosis includes the population of subjects with both acute kidney injury and pulmonary fibrosis.

(2) Measurement of Biomarkers (2.1) Measurement of Protein Markers in Serum

Serum was prepared from the blood initially collected from each subject. Serum levels of IL-6, IL-10, IL-18, CXCL9, CCL3, CCL17, VEGF, SP-A, KL-6, NT-pro-BNP, and P-SEP of each subject were measured by using a fully automated immunoassay system HISCL-5000 (from Sysmex Corporation). The measurement with use of HISCL-5000 was conducted according to the sandwich ELISA method that uses a capture antibody and a detection antibody that specifically binds to each marker, and a magnetic particle as a solid phase. For example, CXCL9 was measured using reagents R1 to R5 below. Also all other markers were measured in the same manner as in the measurement of CXCL9, except that the capture antibody and the detection antibody were changed.

Reagent R1

An anti-MIG monoclonal antibody (from RANDOX) was digested with pepsin or the like by a common method, to obtain a Fab fragment. The Fab fragment was labeled with biotin by a common method, and dissolved in a buffer containing 1% bovine serum albumin (BSA) and 0.5% casein, to obtain reagent R1.

Reagent R2

Magnetic particle having streptavidin immobilized on surface (also referred to as "STA-bound magnetic particle", hereinafter, average particle size: 2 μm, amount of streptavidin per 1 g of magnetic particles: 2.9 to 3.5 mg) was washed three times with a 10 mM HEPES buffer solution (pH 7.5). The washed STA-bound magnetic particle was added to 10 mM HEPES (pH 7.5) so as to adjust the streptavidin concentration to 18 to 22 µg/ml (the STA-bound magnetic particle concentration to 0.48 to 0.52 mg/ml), to obtain reagent R2.

Reagent R3

An anti-MIG monoclonal antibody (from RANDOX) was digested with pepsin or the like by a common method, to obtain a Fab fragment. The Fab fragment was labeled with ALP by a common method, and dissolved in a buffer containing 1% BSA and 0.5% casein, to obtain reagent R3.

Reagent R4 and Reagent R5

HISCL reagent R4 (from Sysmex Corporation), which is a measurement buffer, was used as reagent R4. HISCL reagent R5 (Sysmex Corporation) containing CDP-Star (registered trademark) (from Applied Biosystems), which is a chemiluminescent substrate of ALP, was used as reagent R5.

The measurement procedure with use of HISCL-5000 was as follows. Serum (20 µL) and reagent R1 (50 µL) were mixed, and reagent R2 (30 µL) was then added. The magnetic particle in the obtained liquid mixture was magnetically collected to remove the supernatant, and the magnetic particle was washed by adding HISCL washing solution (300 µL). The supernatant was removed, and reagent R3 (100 µL) was added to the magnetic particle, followed by mixing. The magnetic particle in the obtained liquid mixture was magnetically collected to remove the supernatant, and the magnetic particle was washed by adding HISCL washing solution (300 µL). The supernatant was removed, reagent R4 (50 µL) and reagent R5 (100 µL) were added to the magnetic particle, and chemiluminescence intensity was then measured. A buffer that contains recombinant CXCL9 was used as a calibrator. The calibrator was measured in the same manner as the serum, to prepare a calibration curve. Chemiluminescence intensity obtained by the measurement of each serum was fitted to the calibration curve, to determine CXCL9 level.

(2.2) Measurement of Markers in Blood

CRP, LD, and blood cell counts (lymphocytes and neutrophils) in the blood initially collected from each subject were measured by common methods, and the measured results were recorded in a medical chart. In this example, the measured values of these markers were acquired from the medical chart of each subject.

(3) Cluster Analysis

Figure 5:
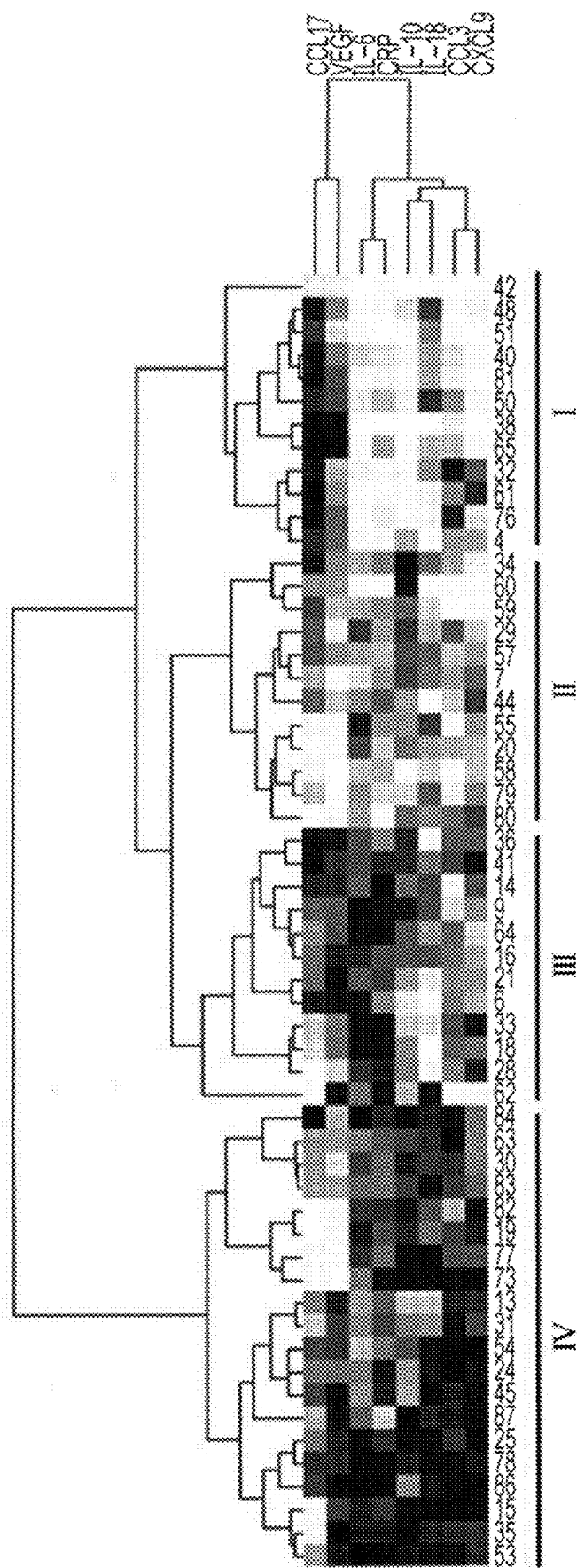
FIG. 5 is a diagram illustrating results of cluster analysis of COVID-19 patients, classified on the basis of levels of CCL17, VEGF (vascular endothelial growth factor), IL-6, CRP (C-reactive protein), IL-10, IL-18, CCL3 and CXCL9.

Fifty-six subjects were classified by unsupervised hierarchical cluster analysis, on the basis of levels of eight markers relevant to inflammation (CCL17, VEGF, IL-6, CRP, IL-10, IL-18, CXCL9 and CCL3). The cluster analysis was conducted according to the complete linkage method based on Euclidean distance, by using Cluster 3.0 (University of Tokyo). The results are illustrated in FIG. 5. As illustrated in FIG. 5, subjects were stratified into four clusters I, II, III, and IV. Cluster I represents a group in which only the CCL17 level was high, Cluster II represents a group in which the levels of the eight markers were generally low, Cluster III represents a group in which the levels of CRP, IL-6 and VEGF were high, and Cluster IV represents a group in which the levels of CXCL9, CCL3, IL-18, IL-10, CRP, IL-6 and VEGF were high.

Figure 6A:
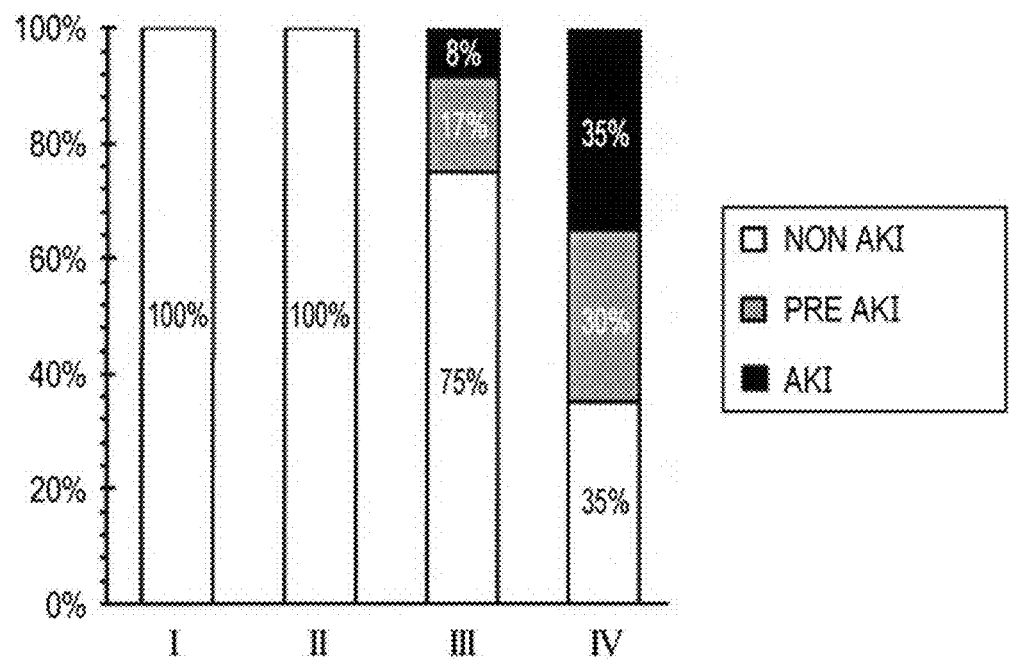
FIG. 6A is a graph illustrating the ratio of subjects having acute kidney injury and subjects having no acute kidney injury in clusters I to IV.
Figure 6B:
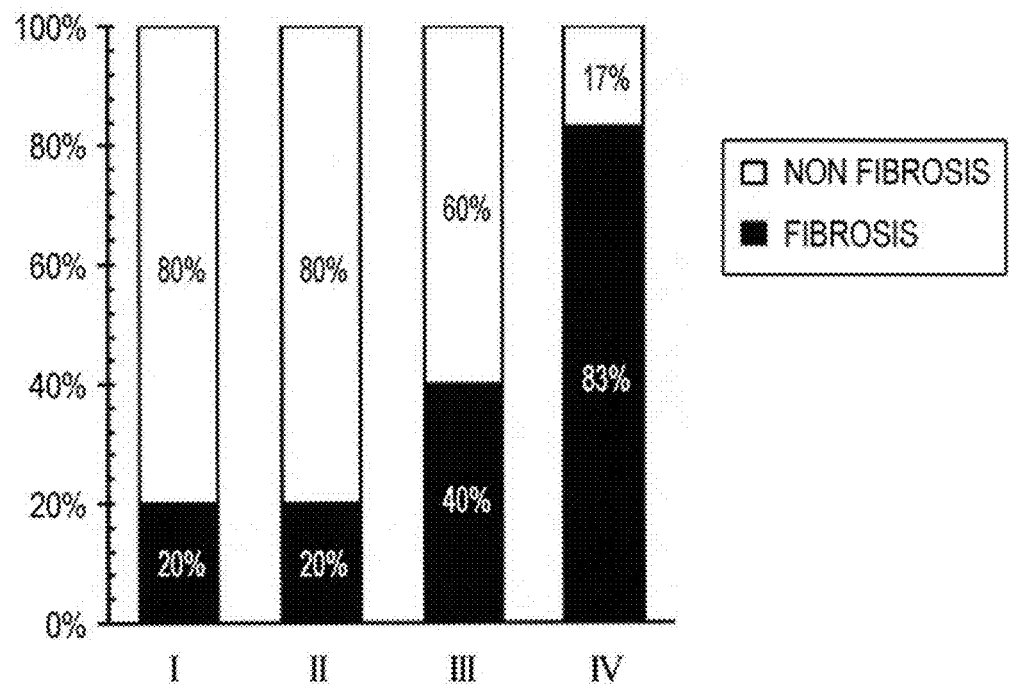
FIG. 6B is a graph illustrating the ratio of subjects having pulmonary fibrosis and subjects having no pulmonary fibrosis in clusters I to IV.

Proportion of subjects with acute kidney injury or pulmonary fibrosis in each cluster was examined. Results are illustrated in FIGS. 6A and 6B. In FIG. 6A, "Non AKI" represents the subjects without the onset of acute kidney injury, "PreAKI" represents the subjects with the onset of acute kidney injury after hospital admission, and "AKI" represents subjects with acute kidney injury having already developed on the day of hospital admission. In FIG. 6B, "Non Fibrosis" represents the subject without the onset of pulmonary fibrosis, and "Fibrosis" represents the subjects with the onset of pulmonary fibrosis. As illustrated in FIG. 6A, cluster IV was found to contain remarkably more subjects with acute kidney injury, than the other clusters. As illustrated in FIG. 6B, cluster IV was found to contain remarkably more subjects with pulmonary fibrosis, than the other clusters.

Subjects with and without the onset of acute kidney injury were respectively classified into cluster IV and non-cluster IV (clusters I to III). From among the subjects with the onset of pulmonary fibrosis, those who retained pulmonary fibrosis even after determined to be SARS-CoV-2 infection negative, and those who did not retain pulmonary fibrosis were respectively classified into cluster IV and non-cluster IV. On the basis of this classification, the sensitivity, specificity, PPV, and NPV when the risk of onset of acute kidney injury following COVID-19 was determined, were calculated. The results are summarized in Tables 1 and 2. Similarly, the sensitivity, specificity, PPV, and NPV when the risk of remaining of pulmonary fibrosis following COVID-19 was determined, were calculated. The results are summarized in Table 3. P values listed in Tables 1 to 3 were calculated on the basis of the Fisher's exact test.

TABLE 1

|  | AKI/PreAKI | Non AKI | Total |
| --- | --- | --- | --- |
| Other than cluster IV | 3 | 33 | 36 |
| Cluster IV | 13 | 7 | 20 |
| Total | 16 | 40 |  |
| Sensitivity |  | 81% |  |
| Specificity |  | 83% |  |
| PPV |  | 65% |  |
| NPV |  | 92% |  |

P < 0.0001

TABLE 2

|  | PreAKI | Non AKI | Total |
| --- | --- | --- | --- |
| Other than cluster IV | 2 | 33 | 35 |
| Cluster IV | 6 | 7 | 13 |
| Total | 8 | 40 |  |
| Sensitivity |  | 75% |  |
| Specificity |  | 83% |  |
| PPV |  | 46% |  |
| NPV |  | 94% |  |

P = 0.0028

TABLE 3

|  | Fibrosis retained | Fibrosis not retained | Total |
| --- | --- | --- | --- |
| Other than cluster IV | 4 | 11 | 15 |
| Cluster IV | 10 | 3 | 13 |
| Total | 14 | 14 |  |
| Sensitivity |  | 71% |  |
| Specificity |  | 79% |  |
| PPV |  | 77% |  |
| NPV |  | 73% |  |

P = 0.021

The results summarized in Table 1 to 3 suggested that the subjects who belong to Cluster IV had a higher risk of causing acute kidney injury following respiratory infection and a higher risk of remaining pulmonary fibrosis, than the subjects who belong to other than Cluster IV. Therefore, it was suggested that a biomarker capable of discriminating between Cluster IV and other than Cluster IV (particularly Cluster III) is useful for determining the risk of causing acute kidney injury and pulmonary fibrosis following respiratory infection.

(4) Comparison of Measured Values of Biomarkers Among Clusters

Figure 7:
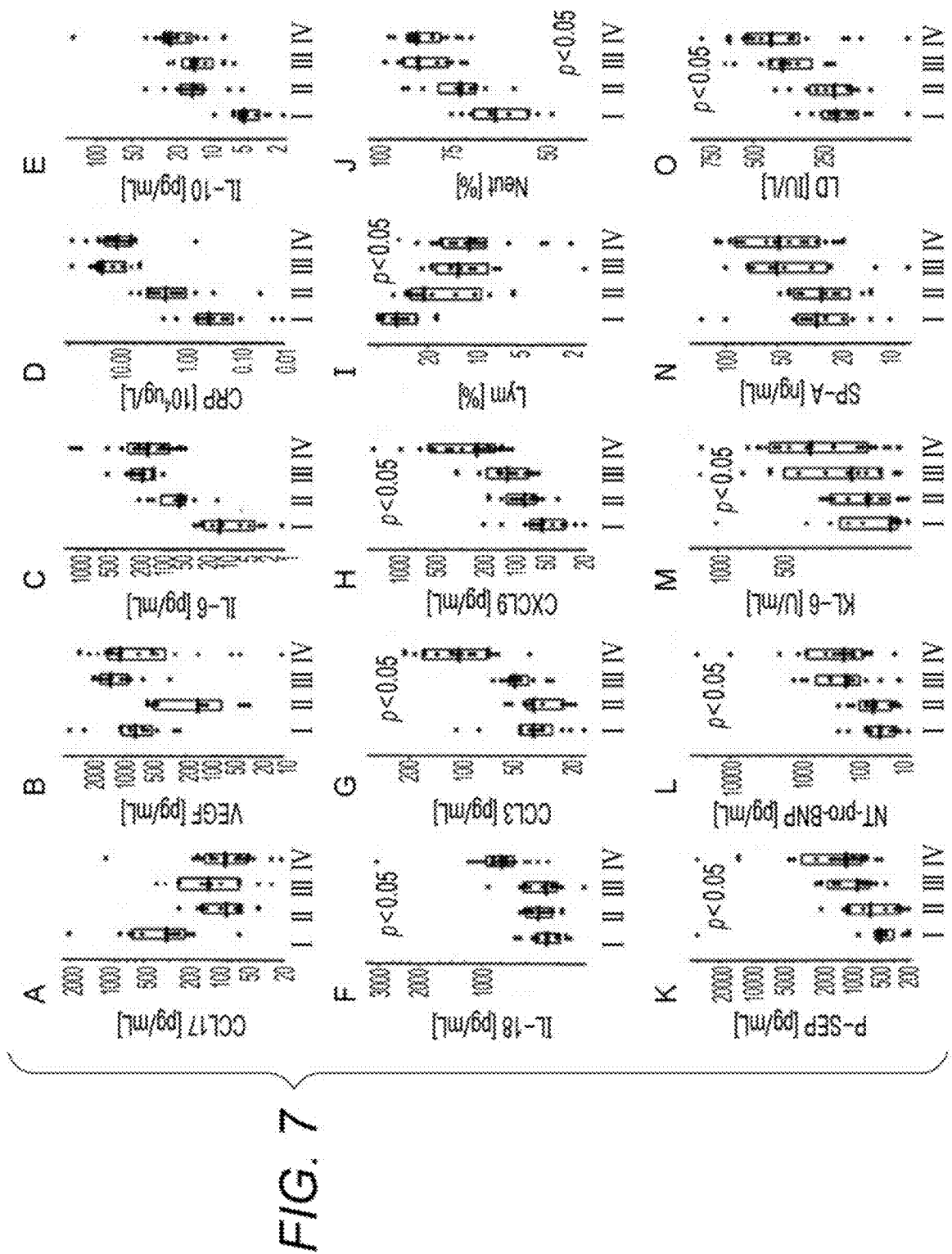
FIG. 7 is a box plot illustrating distributions of measured values of CCL17, VEGF, IL-6, CRP, IL-10, IL-18, CCL3, CXCL9, lymphocytes (Lym), neutrophils (Neut), P-SEP (presepsin), NT-pro-BNP (brain sodium peptide), KL-6 (Krebs von den Lungen-6), SP-A (surfactant protein A), and LD (lactose dehydrogenase) in clusters I to IV.

Levels of the individual biomarkers in clusters I to IV are summarized in FIG. 7. In the drawing, "Lym" represents lymphocyte, and "Neut" represents neutrophil. From among the fifteen markers, IL-18, CCL3, and CXCL9 demonstrated significantly higher values in cluster IV, than in clusters I to III, as illustrated respectively in F, G, and H of FIG. 7. This result suggests that CXCL9, CCL3, and IL-18 can serve as the biomarkers for determining the risk of causing acute kidney injury or pulmonary fibrosis following respiratory infection.

IL-6 and CRP demonstrated significantly higher values in clusters III and IV, than in clusters I and II, as illustrated respectively in C and D in FIG. 7. On the other hand, the measured values of IL-6 and CRP demonstrated no significant difference between clusters III and IV. These results suggested that IL-6 and CRP are useful for determining the risk of causing acute kidney injury or pulmonary fibrosis following respiratory infection, when used in combination with CXCL9, CCL3, and IL-18.

(5) Monitoring of Measured Values of Biomarkers

Serum was prepared from blood collected from each subject at multiple time points during the hospital admission, and six biomarkers (CXCL9, CCL3, IL-18, IL-6, CRP and LD) were measured. Graphs were created by plotting the measured values of the biomarkers of the subjects (Non AKI) without the onset of acute kidney injury, the subjects (PreAKI) with the onset of acute kidney injury after hospital admission, and the subjects (AKI) with acute kidney injury having already developed on the day of hospital admission. The results are summarized in FIGS. 8A to 8F. The measured value of the individual biomarkers of the subject who did not retain pulmonary fibrosis even after determined to be SARS-CoV-2 infection negative (Non Fibrosis), and the subjects who retained pulmonary fibrosis (Fibrosis) were plotted to prepare graphs. The results are summarized in FIGS. 9A to 9F. Among subjects with PreAKI and AKI, subjects whose serum creatinine level on the day of hospital admission was higher than the reference value were classified into subjects with a high creatinine level, and subjects whose serum creatinine level on the day of hospital admission was equal to or lower than the reference value were classified into subjects with normal creatinine level.

Figure 8A:
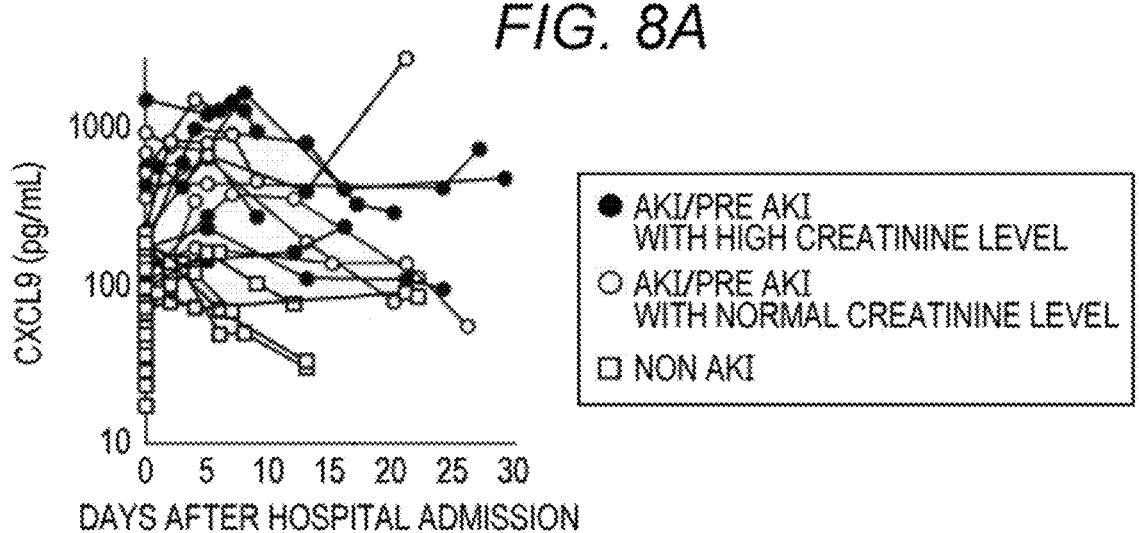
FIG. 8A is a graph illustrating transitions of serum CXCL9 levels of subjects having acute kidney injury and subjects having no acute kidney injury.
Figure 8B:
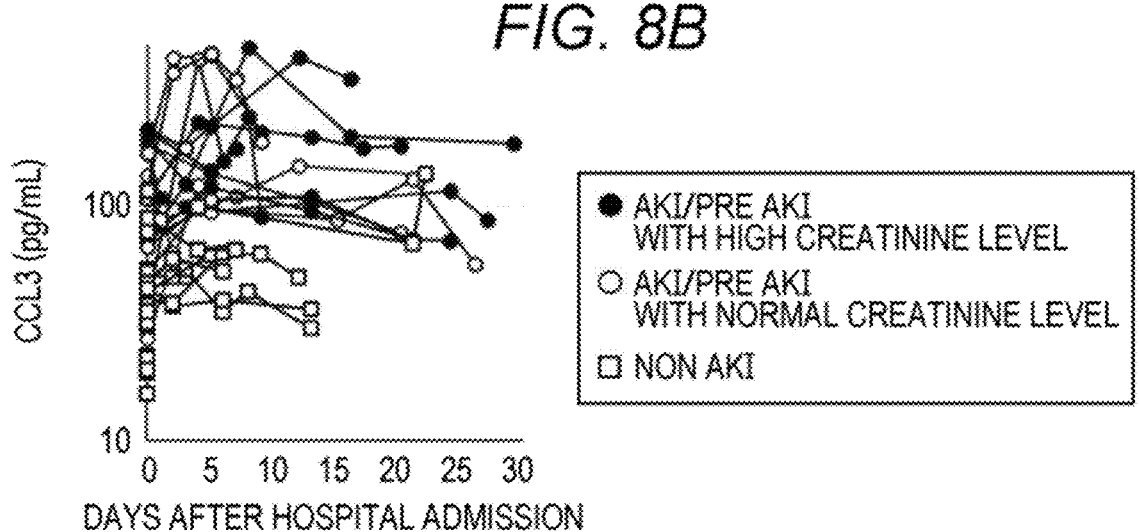
FIG. 8B is a graph illustrating transitions of serum CCL3 levels of subjects having acute kidney injury and subjects having no acute kidney injury.
Figure 8C:
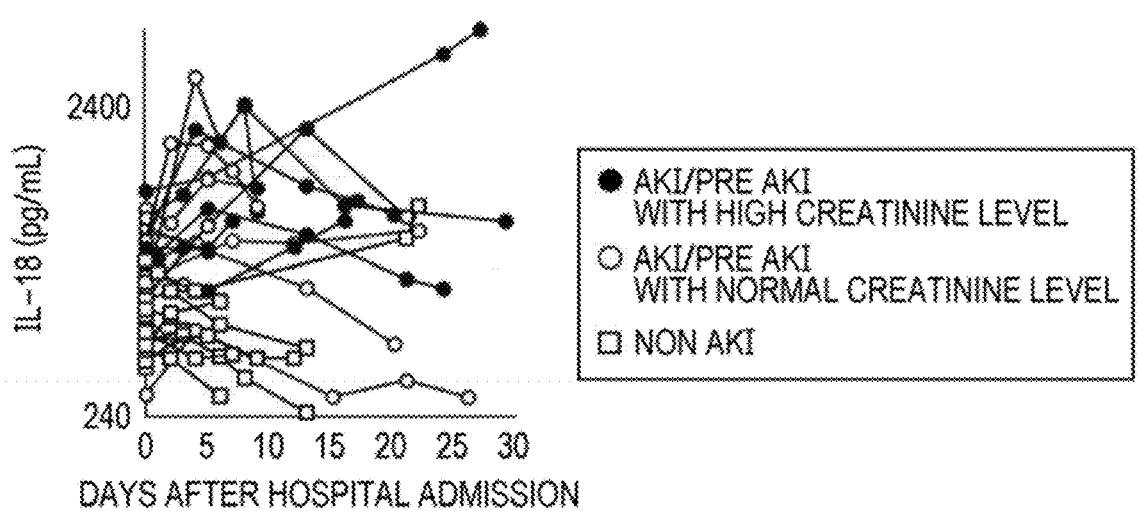
FIG. 8C is a graph illustrating transitions of serum IL-18 levels of subjects having acute kidney injury and subjects having no acute kidney injury.
Figure 8D:
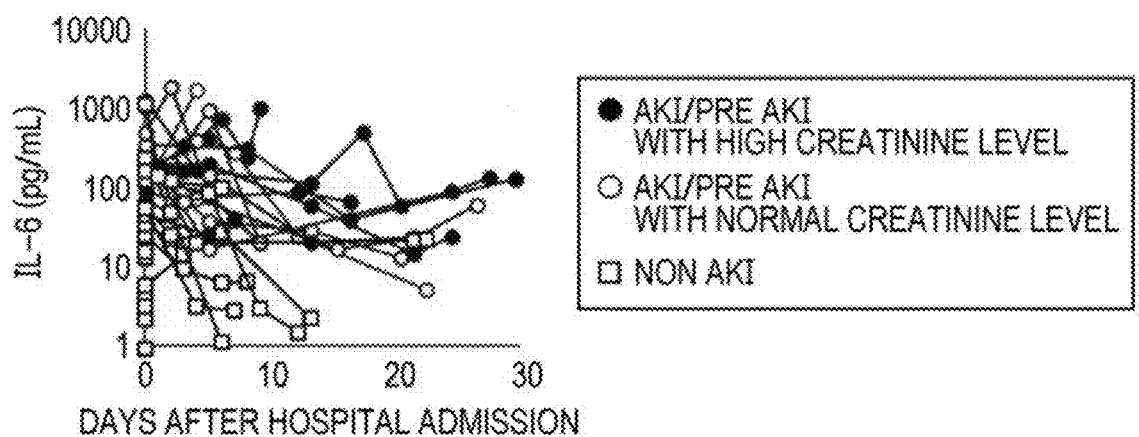
FIG. 8D is a graph illustrating transitions of serum IL-6 levels of subjects having acute kidney injury and subjects having no acute kidney injury.
Figure 8E:
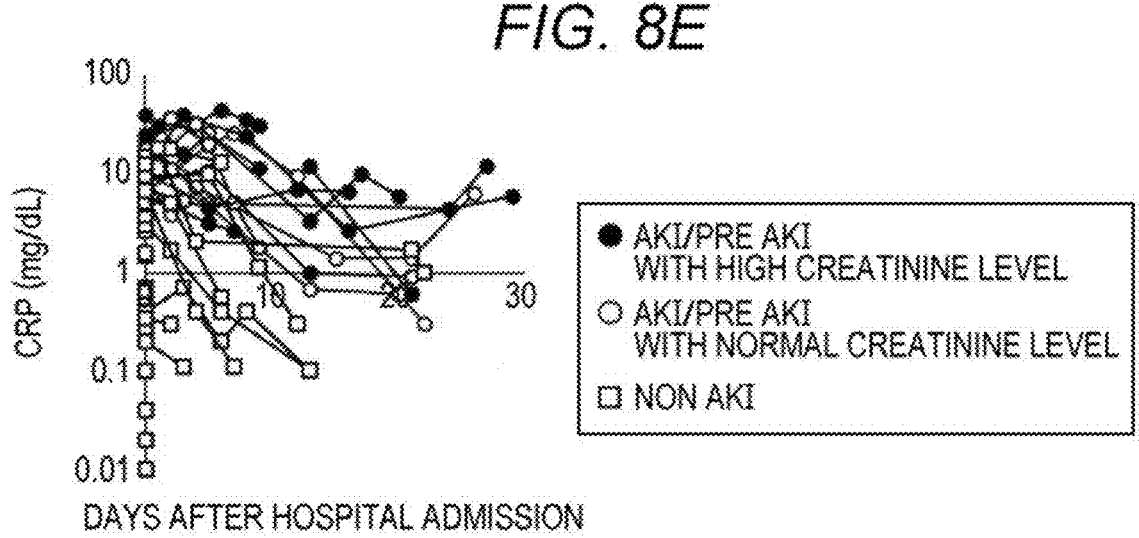
FIG. 8E is a graph illustrating transitions of blood CRP levels of subjects having acute kidney injury and subjects having no acute kidney injury.
Figure 8F:
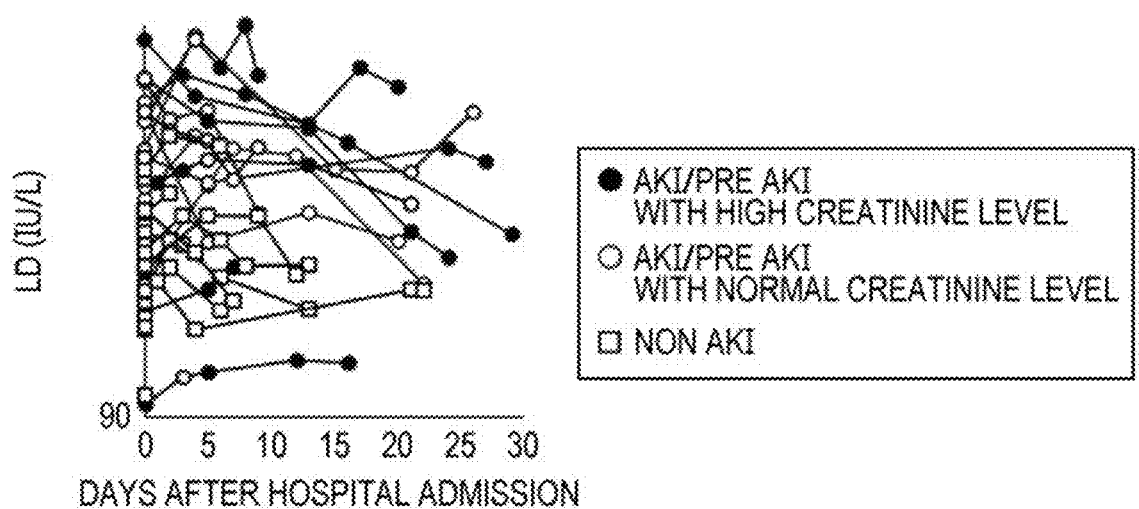
FIG. 8F is a graph illustrating transitions of blood LD levels of subjects having acute kidney injury and subjects having no acute kidney injury.

As illustrated in FIGS. 8A to 8C, the measured values of CXCL9, CCL3, and IL-18 of the subjects with PreAKI and AKI were found to be higher overall than those of the subjects with Non AKI during the hospital admission, regardless whether the serum creatinine level was high or normal. On the other hand, as illustrated in FIGS. 8D to 8F, the measured values of IL-6, CRP and LD of the subjects with PreAKI and AKI were found to decline overall with the elapse of days, even if the serum creatinine level was high.

Figure 9A:
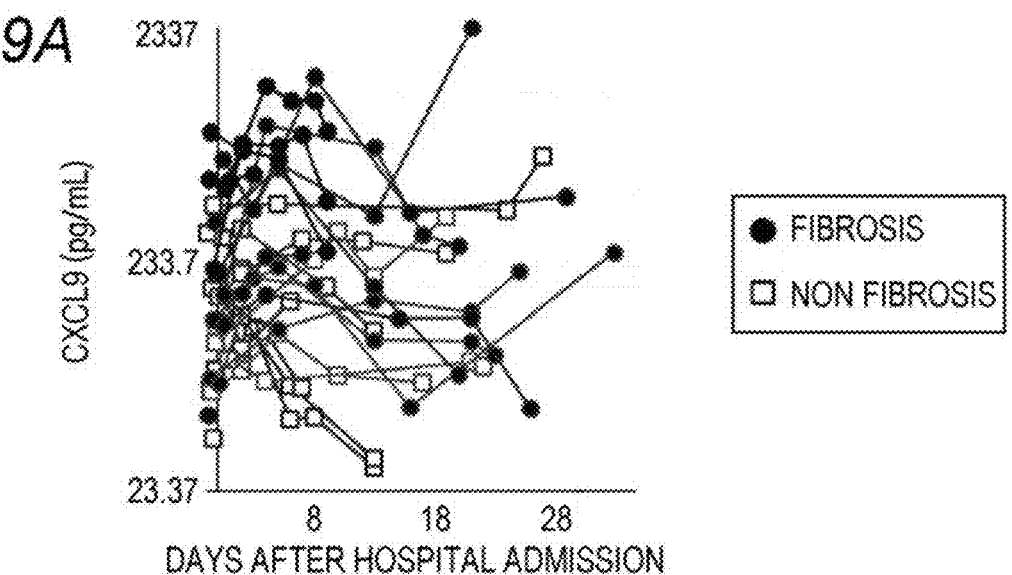
FIG. 9A is a graph illustrating transitions of serum CXCL9 levels of subjects having pulmonary fibrosis and subjects having no pulmonary fibrosis.
Figure 9B:
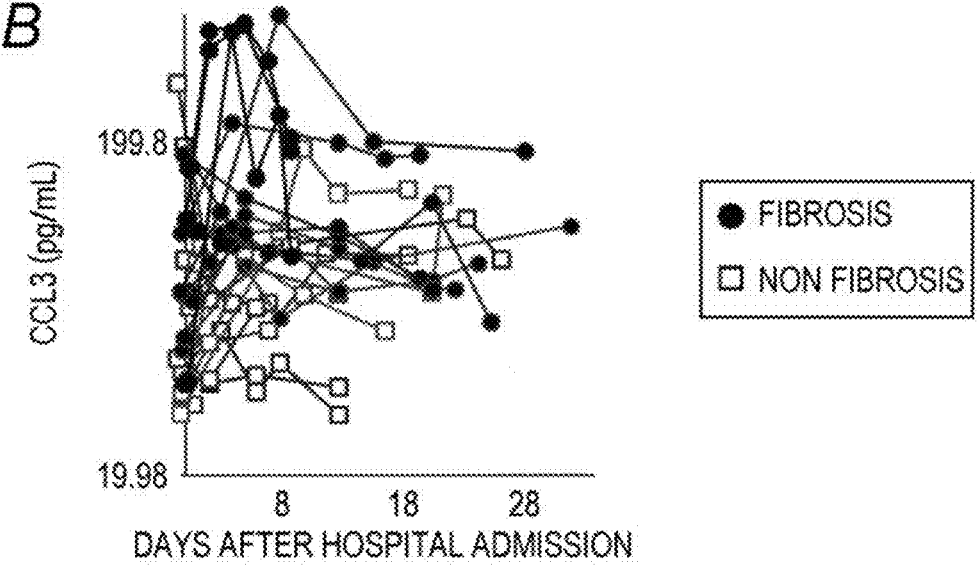
FIG. 9B is a graph illustrating transitions of serum CCL3 levels of subjects having pulmonary fibrosis and subjects having no pulmonary fibrosis.
Figure 9C:
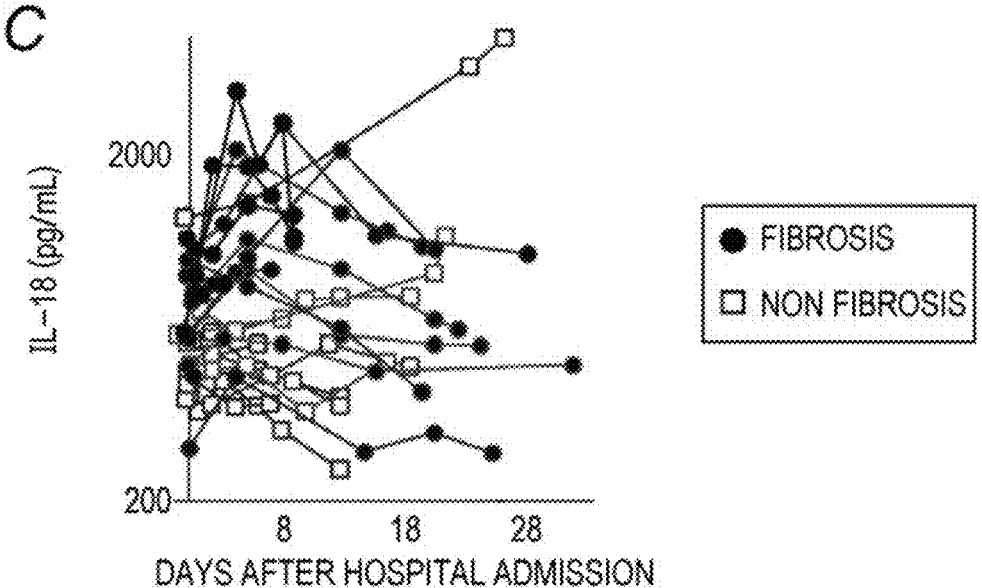
FIG. 9C is a graph illustrating transitions of serum IL-18 levels of subjects having pulmonary fibrosis and subjects having no pulmonary fibrosis.
Figure 9D:
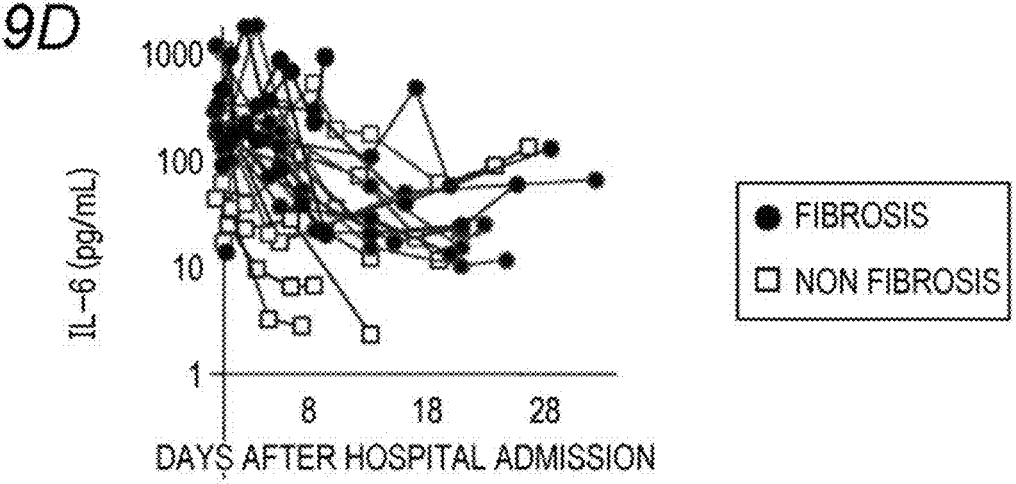
FIG. 9D is a graph illustrating transitions of serum IL-6 levels of subjects having pulmonary fibrosis and subjects having no pulmonary fibrosis.
Figure 9E:
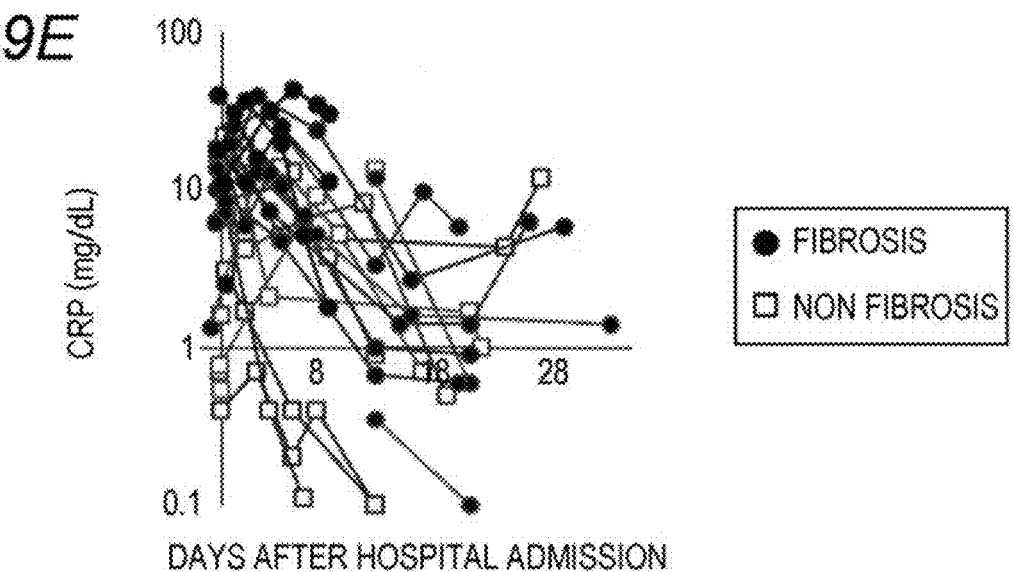
FIG. 9E is a graph illustrating transitions of blood CRP levels of subjects having pulmonary fibrosis and subjects having no pulmonary fibrosis.
Figure 9F:
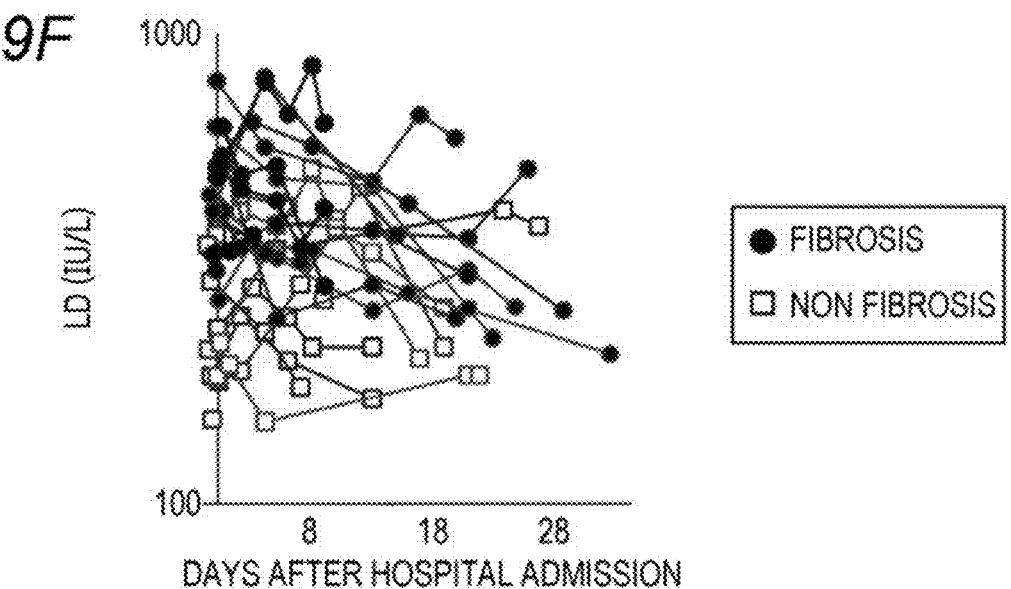
FIG. 9F is a graph illustrating transitions of blood LD levels of subjects having pulmonary fibrosis and subjects having no pulmonary fibrosis.

As illustrated in FIGS. 9A to 9C, the measured values of CXCL9, CCL3 and IL-18 of the subjects who retain the pulmonary fibrosis (Fibrosis) were found to be higher overall than those of the subjects who did not retain pulmonary fibrosis (Non Fibrosis) during the period of hospital admission. On the other hand, as illustrated in FIGS. 9D to 9F, no significant differences in the measured values of IL-6, CRP and LD were found between the subjects who retained pulmonary fibrosis (Fibrosis) and the subjects who did not retain pulmonary fibrosis (Non Fibrosis).

What is claimed is:

1. A method for acquiring information on respiratory infection of a subject and treating the subject, the method comprising:
   measuring CXC chemokine ligand 9 (CXCL9) in a specimen collected from the subject suffering from a respiratory infection, or from the subject suspected of having the respiratory infection;
   determining a risk of causing acute kidney injury following respiratory infection, on the basis of a measured value of CXCL9, and
   treating the subject who is determined to have high risk of acute kidney injury with at least one medical intervention selected from the group consisting of administration of a drug, dialysis, surgery, immunotherapy, and gene therapy.

2. The method according to claim 1, wherein the measured value of CXCL9, if found to be equal to or exceeding a predetermined threshold value that corresponds to CXCL9, determines a high risk of causing acute kidney injury following respiratory infection.

3. The method according to claim 1, wherein the measured value of CXCL9, if found to be lower than a predetermined threshold value that corresponds to CXCL9, determines a low risk of causing acute kidney injury following respiratory infection.

4. The method according to claim 1, wherein the specimen is whole blood, plasma, or serum.

5. The method according to claim 1, wherein the respiratory infection is an infection caused by severe acute respiratory syndrome coronavirus 2 (SARS-CoV-2), severe acute respiratory syndrome coronavirus (SARS-CoV), or middle east respiratory syndrome coronavirus (MERS-CoV).

6. The method according to claim 1, wherein the drug comprises at least one selected from the group consisting of a steroid drug, an immunosuppressive drug and an antifibrotic drug.

7. A method for acquiring information on respiratory infection of a subject and treating the subject, the method comprising:
   measuring CXCL9 and interleukin-18 (IL-18) in a specimen collected from the subject suffering from a respiratory infection, or from the subject suspected of having the respiratory infection;
   determining a risk of causing acute kidney injury or pulmonary fibrosis following respiratory infection, on the basis of a measured value of CXCL9 and a measured value of IL-18; and
   treating the subject who is determined to have high risk of causing the acute kidney injury or the pulmonary fibrosis with at least one medical intervention selected from the group consisting of administration of a drug, dialysis, surgery, immunotherapy, gene therapy, oxygenation therapy, and therapy with a cardiopulmonary bypass.

8. The method according to claim 7, wherein the specimen is whole blood, plasma, or serum.

9. The method according to claim 7, wherein the respiratory infection is an infection caused by SARS-CoV-2, SARS-CoV, or MERS-CoV.

10. The method according to claim 7, wherein the drug comprises at least one selected from the group consisting of a steroid drug, an immunosuppressive drug and an anti-fibrotic drug.

11. The method according to claim 7, wherein the measured value of at least CXCL9 or IL-18, if found to be equal to or exceeding a predetermined threshold value that corresponds to the biomarker, determines a high risk of causing acute kidney injury following respiratory infection.

12. The method according to claim 7, wherein the measured values of CXCL9 and IL-18, if all found to be lower than predetermined threshold values that correspond to the biomarkers, determine a low risk of causing acute kidney injury following respiratory infection.

* * * * *